(12) United States Patent
Barbieri et al.

(10) Patent No.: US 7,588,587 B2
(45) Date of Patent: Sep. 15, 2009

(54) SUTURE ANCHORS

(75) Inventors: Thomas J. Barbieri, Hamden, CT (US); Jonathan Martinek, Cheshire, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 346 days.

(21) Appl. No.: 11/371,821

(22) Filed: Mar. 9, 2006

(65) Prior Publication Data

US 2006/0276841 A1 Dec. 7, 2006

Related U.S. Application Data

(60) Provisional application No. 60/660,499, filed on Mar. 10, 2005.

(51) Int. Cl.
*A61B 17/04* (2006.01)

(52) U.S. Cl. ..................................................... 606/232

(58) Field of Classification Search ................. 606/232, 606/300, 302
See application file for complete search history.

(56) References Cited

U.S. PATENT DOCUMENTS

| | | | |
|---|---|---|---|
| 4,259,072 A | 3/1981 | Hirabayashi et al. | |
| 4,454,875 A | 6/1984 | Pratt et al. | |
| 4,570,623 A | 2/1986 | Ellison et al. | |
| 4,738,255 A | 4/1988 | Goble et al. | |
| 4,772,286 A | 9/1988 | Goble et al. | |
| 4,870,957 A * | 10/1989 | Goble et al. | 623/13.12 |
| 4,895,148 A * | 1/1990 | Bays et al. | 606/213 |
| 4,927,421 A | 5/1990 | Goble et al. | |
| 4,950,270 A | 8/1990 | Bowman et al. | |
| 5,013,316 A | 5/1991 | Goble et al. | |
| 5,019,080 A | 5/1991 | Hemer | |
| 5,100,417 A * | 3/1992 | Cerier et al. | 606/139 |
| 5,122,133 A | 6/1992 | Evans | |
| 5,156,616 A | 10/1992 | Meadows et al. | |
| 5,176,682 A | 1/1993 | Chow | |
| RE34,293 E | 6/1993 | Goble et al. | |
| 5,258,001 A | 11/1993 | Corman | |
| 5,258,016 A | 11/1993 | DiPoto et al. | |
| 5,320,115 A | 6/1994 | Kenna | |
| 5,354,298 A | 10/1994 | Lee et al. | |
| 5,370,662 A * | 12/1994 | Stone et al. | 606/232 |
| 5,372,599 A | 12/1994 | Martins | |
| 5,383,878 A | 1/1995 | Roger et al. | |
| 5,383,905 A * | 1/1995 | Golds et al. | 606/232 |
| 5,387,129 A | 2/1995 | Hotea | |
| RE34,871 E | 3/1995 | McGuire et al. | |
| 5,417,712 A | 5/1995 | Whittaker et al. | |
| 5,423,860 A * | 6/1995 | Lizardi et al. | 606/232 |

(Continued)

OTHER PUBLICATIONS

International Search Report for PCT/US06/08547 date of completion is Apr. 16, 2008 (9 pages).

*Primary Examiner*—Darwin P Erezo

(57) ABSTRACT

A suture anchor includes an outer sleeve having a longitudinal throughbore and defining leading and trailing ends and an insert positionable within the longitudinal throughbore of the outer sleeve. The insert defines at least one suture track for slidably supporting a suture whereby opposed free ends of the suture extend from the at least one suture track through the longitudinal throughbore to extend beyond the trailing end of the outer sleeve to be tensioned and secured relative to the tissue. The outer sleeve may include an external thread for threaded rotation and advancement into the tissue.

14 Claims, 31 Drawing Sheets

U.S. PATENT DOCUMENTS

| | | | |
|---|---|---|---|
| 5,425,733 A | 6/1995 | Schmieding | |
| 5,443,482 A | 8/1995 | Stone et al. | |
| 5,443,509 A | 8/1995 | Boucher et al. | |
| 5,456,685 A | 10/1995 | Huebner | |
| 5,464,427 A * | 11/1995 | Curtis et al. | 606/232 |
| 5,472,452 A | 12/1995 | Trott | |
| 5,480,403 A * | 1/1996 | Lee et al. | 606/232 |
| 5,522,845 A | 6/1996 | Wenstrom, Jr. | |
| 5,545,180 A * | 8/1996 | Le et al. | 606/232 |
| 5,569,206 A * | 10/1996 | Gorman et al. | 604/167.01 |
| 5,571,139 A | 11/1996 | Jenkins, Jr. | |
| 5,573,548 A | 11/1996 | Nazre et al. | |
| 5,584,835 A * | 12/1996 | Greenfield | 606/232 |
| 5,584,836 A | 12/1996 | Ballintyn et al. | |
| 5,603,716 A | 2/1997 | Morgan et al. | |
| 5,645,547 A | 7/1997 | Coleman | |
| 5,690,676 A | 11/1997 | DiPoto et al. | |
| 5,702,397 A | 12/1997 | Goble et al. | |
| 5,723,013 A * | 3/1998 | Jeanson et al. | 623/17.16 |
| 5,733,307 A | 3/1998 | Dinsdale | |
| 5,735,867 A * | 4/1998 | Golser et al. | 606/185 |
| 5,782,866 A | 7/1998 | Wenstrom, Jr. | |
| 5,824,011 A | 10/1998 | Stone et al. | |
| 5,871,504 A | 2/1999 | Eaton et al. | |
| 5,885,294 A | 3/1999 | Pedlick et al. | |
| 5,904,704 A | 5/1999 | Goble et al. | |
| 5,911,721 A * | 6/1999 | Nicholson et al. | 606/326 |
| RE36,289 E * | 8/1999 | Le et al. | 606/232 |
| 5,941,882 A | 8/1999 | Jammet et al. | |
| 5,944,724 A | 8/1999 | Lizardi | |
| 5,948,000 A | 9/1999 | Larsen et al. | |
| 5,948,001 A | 9/1999 | Larsen | |
| 5,957,953 A * | 9/1999 | DiPoto et al. | 606/232 |
| 5,993,451 A | 11/1999 | Burkhart | |
| 6,045,573 A | 4/2000 | Wenstrom, Jr. et al. | |
| 6,086,608 A * | 7/2000 | Ek et al. | 606/232 |
| 6,096,060 A | 8/2000 | Fitts et al. | |
| 6,117,162 A | 9/2000 | Schmieding et al. | |
| 6,139,565 A | 10/2000 | Stone et al. | |
| 6,146,407 A | 11/2000 | Krebs | |
| 6,146,408 A | 11/2000 | Bartlett | |
| 6,149,669 A | 11/2000 | Li | |
| 6,200,329 B1 * | 3/2001 | Fung et al. | 606/232 |
| 6,214,031 B1 | 4/2001 | Schmieding et al. | |
| 6,235,057 B1 | 5/2001 | Roger et al. | |
| 6,336,940 B1 | 1/2002 | Graf et al. | |
| 6,371,124 B1 | 4/2002 | Whelan | |
| 6,436,100 B1 | 8/2002 | Berger | |
| 6,436,124 B1 | 8/2002 | Anderson et al. | |
| 6,461,373 B2 | 10/2002 | Wyman et al. | |
| 6,517,542 B1 | 2/2003 | Papay et al. | |
| 6,585,730 B1 * | 7/2003 | Foerster | 606/32 |
| 6,629,977 B1 | 10/2003 | Wolf | |
| 6,652,563 B2 * | 11/2003 | Dreyfuss | 606/232 |
| 6,663,656 B2 * | 12/2003 | Schmieding et al. | 606/232 |
| 6,666,877 B2 | 12/2003 | Morgan et al. | |
| 6,840,953 B2 * | 1/2005 | Martinek | 606/232 |
| 7,090,690 B2 * | 8/2006 | Foerster et al. | 606/232 |
| 2001/0041937 A1 | 11/2001 | Rieser et al. | |
| 2002/0147463 A1 * | 10/2002 | Martinek | 606/232 |
| 2002/0161401 A1 | 10/2002 | Steiner | |
| 2003/0065361 A1 | 4/2003 | Dreyfuss | |
| 2003/0125749 A1 | 7/2003 | Yuan et al. | |
| 2003/0195563 A1 * | 10/2003 | Foerster | 606/232 |
| 2004/0097945 A1 | 5/2004 | Wolf | |

* cited by examiner

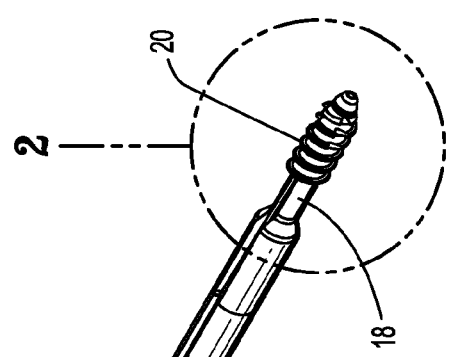
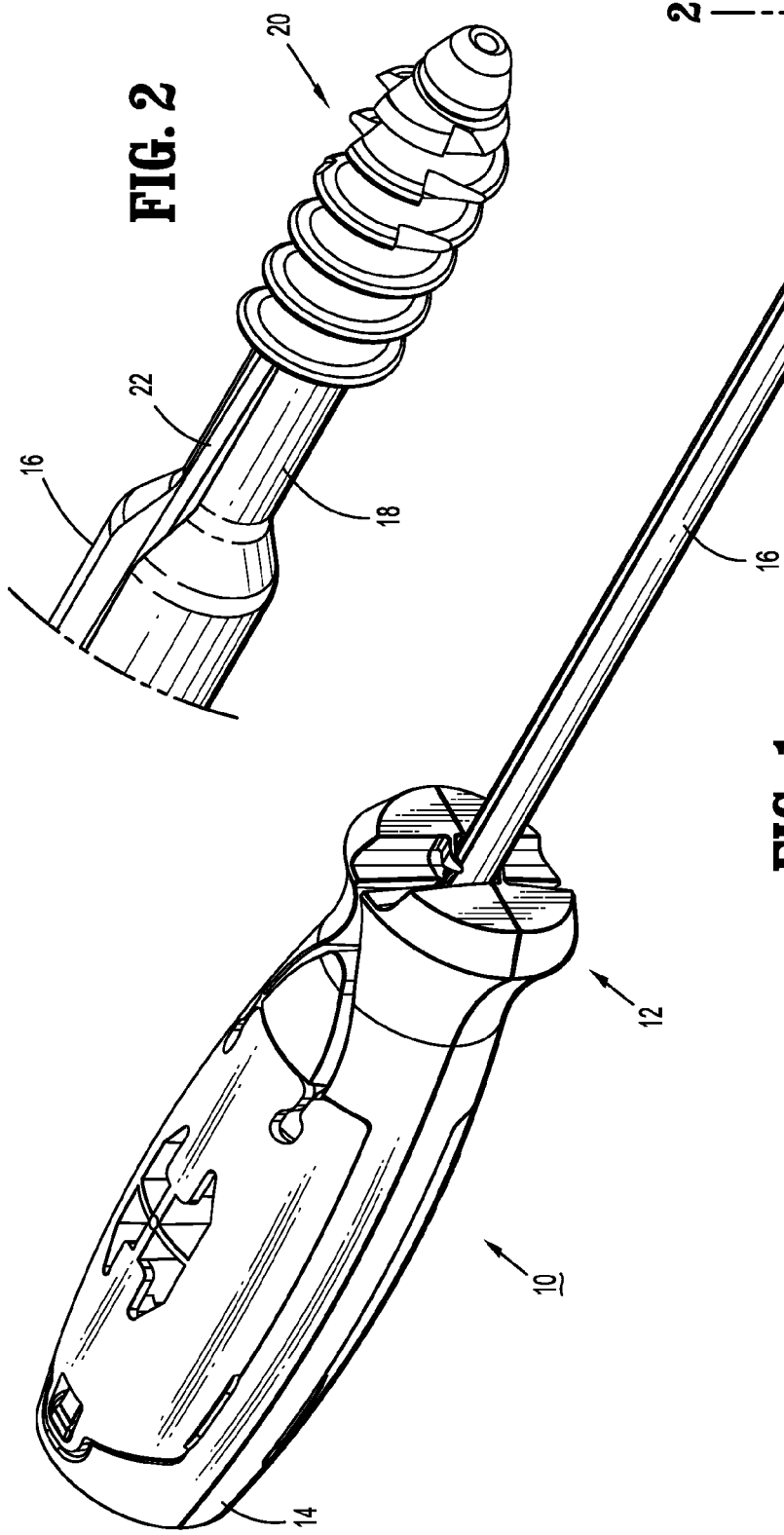
FIG. 2
FIG. 1

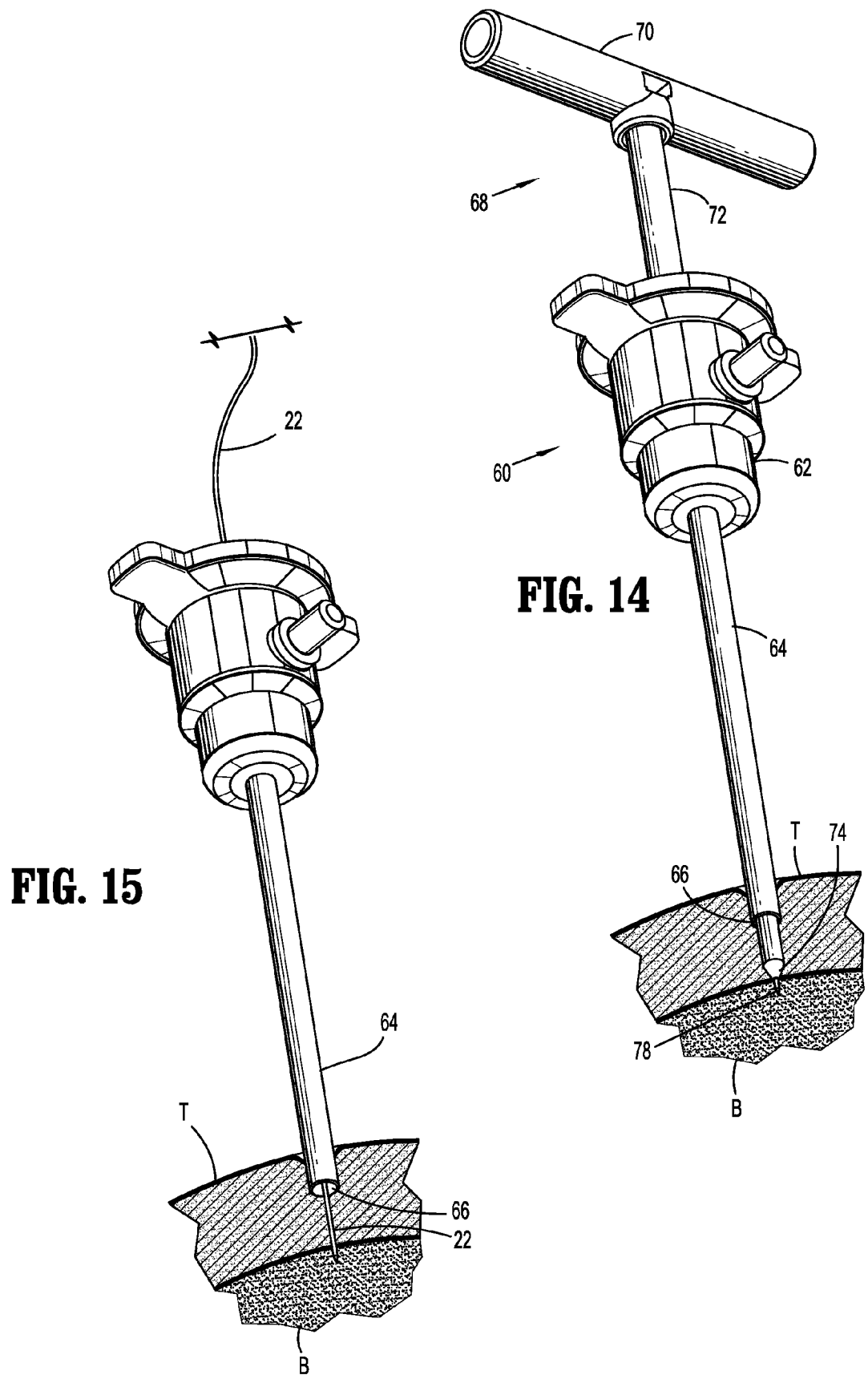

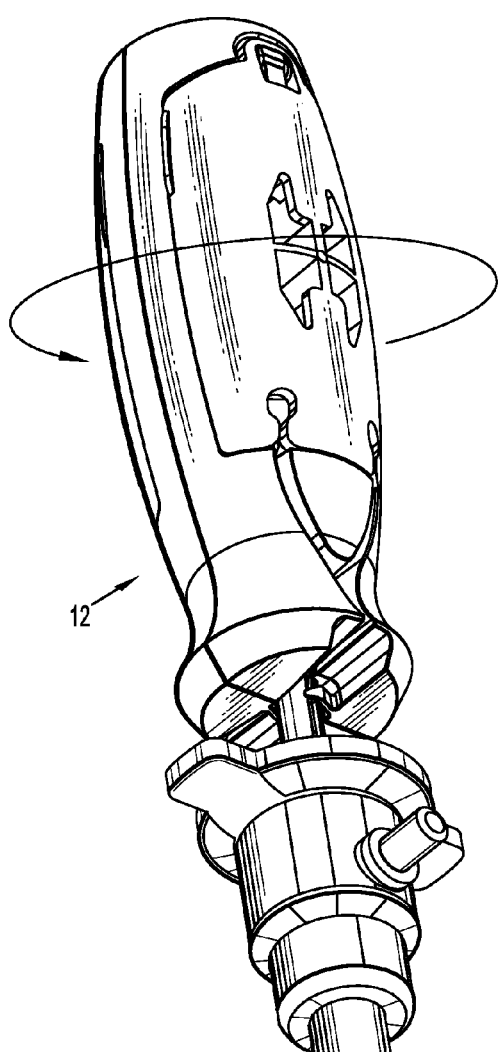
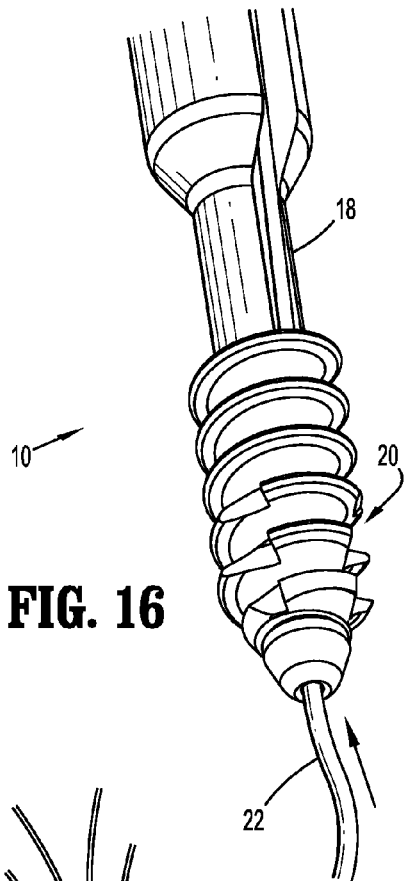
FIG. 16
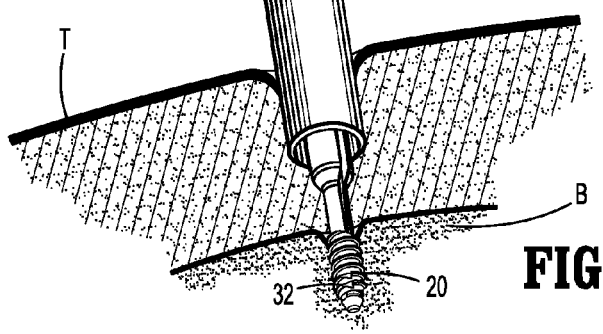
FIG. 18
FIG. 17

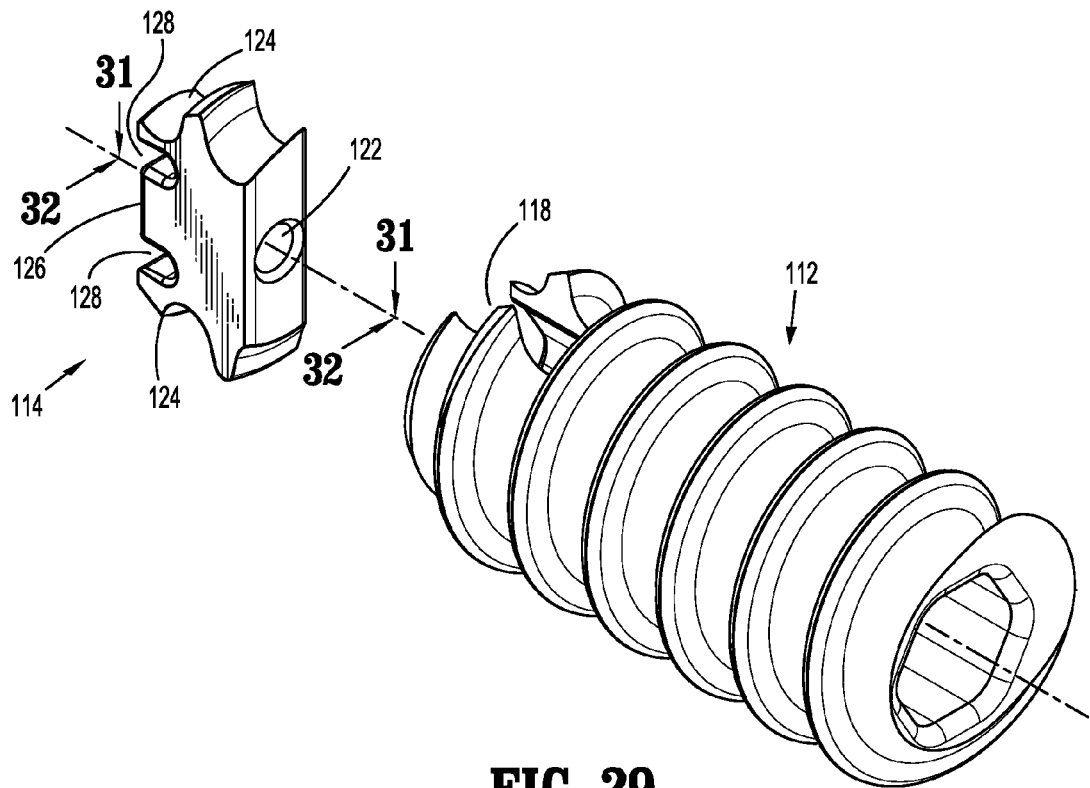
FIG. 29
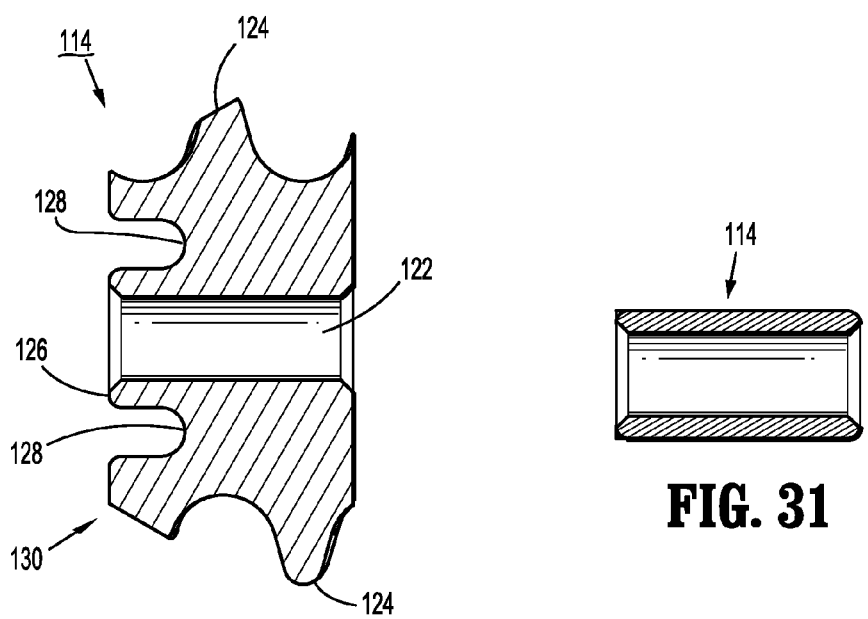
FIG. 30
FIG. 31

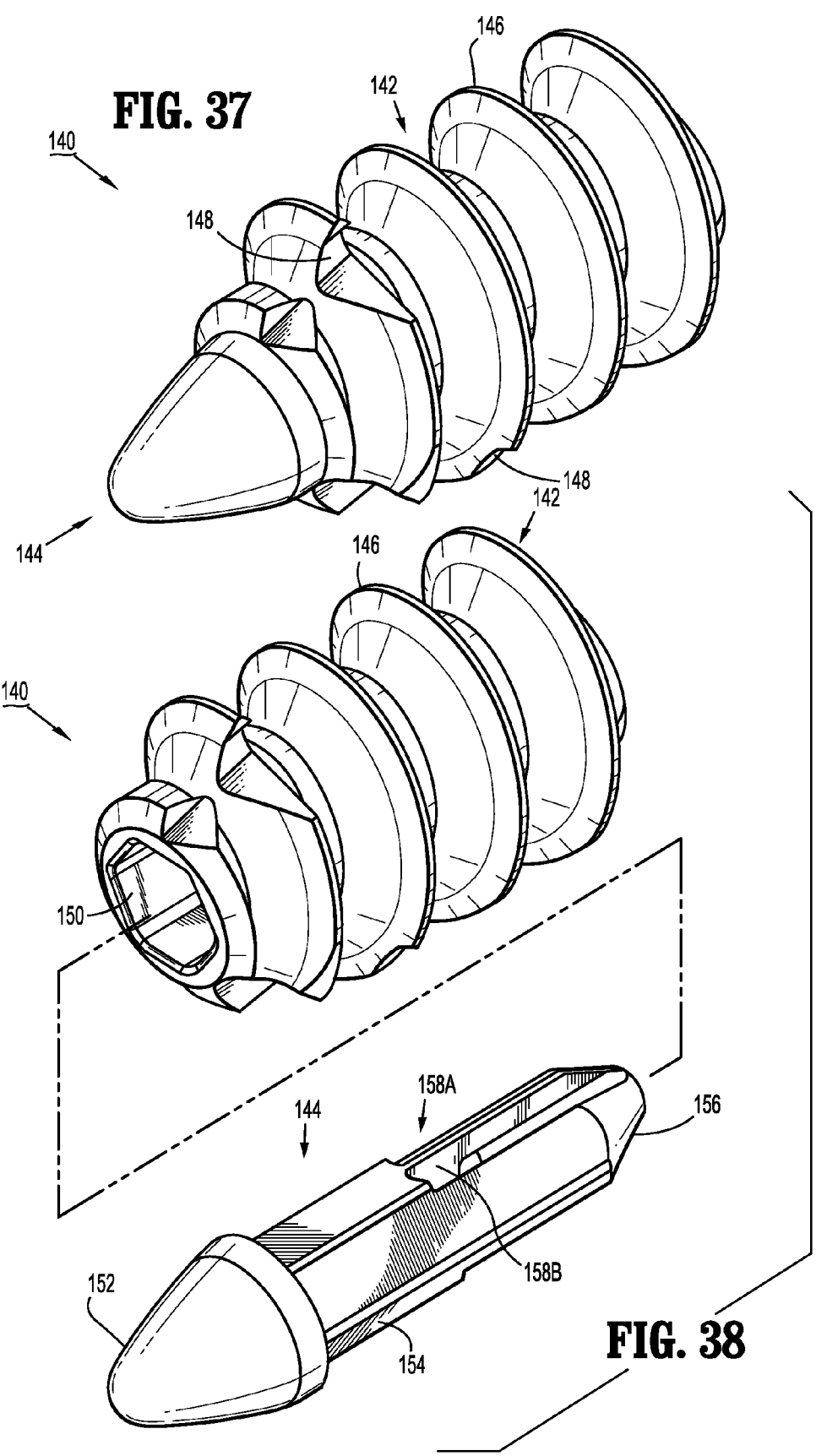

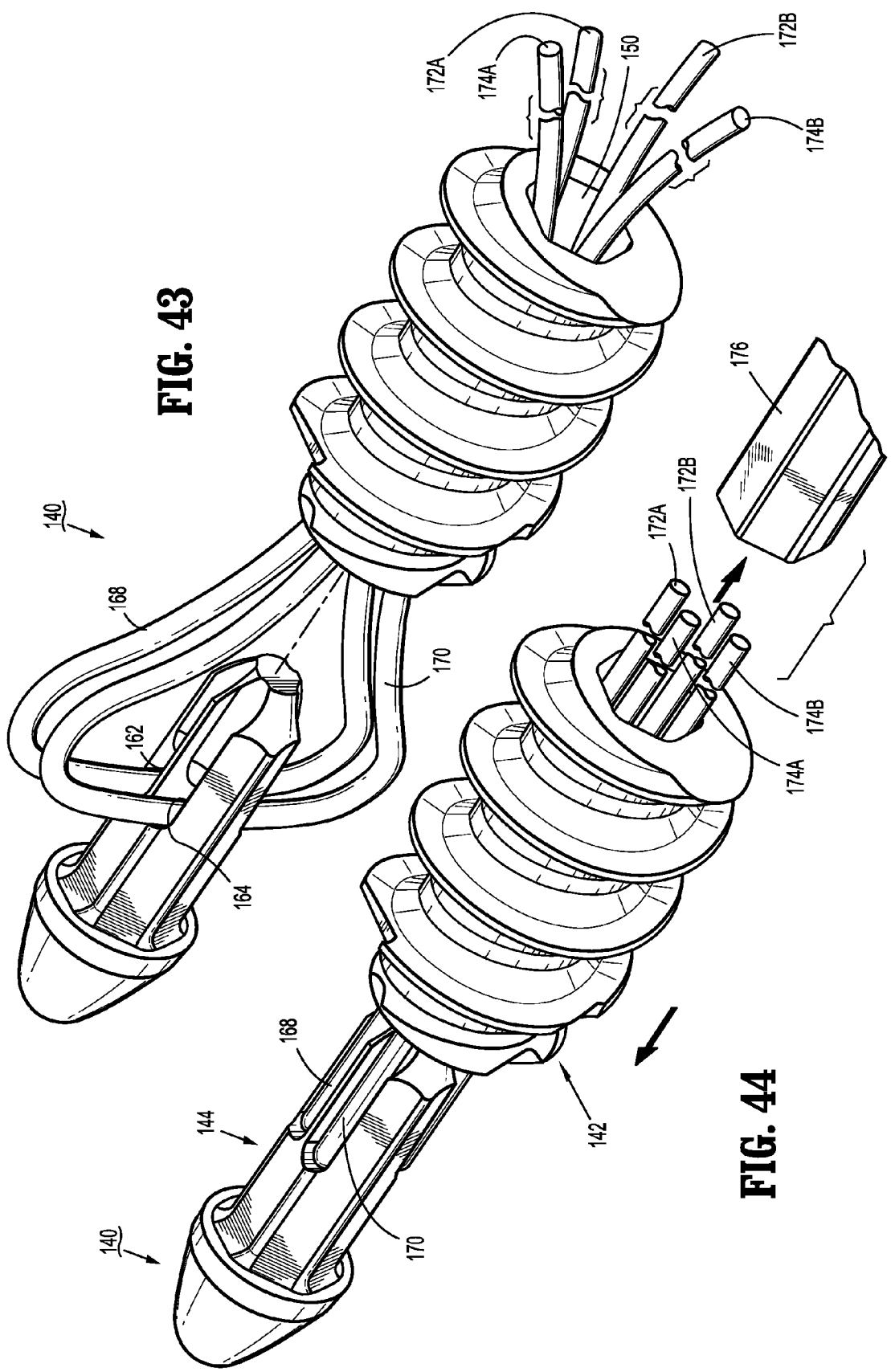

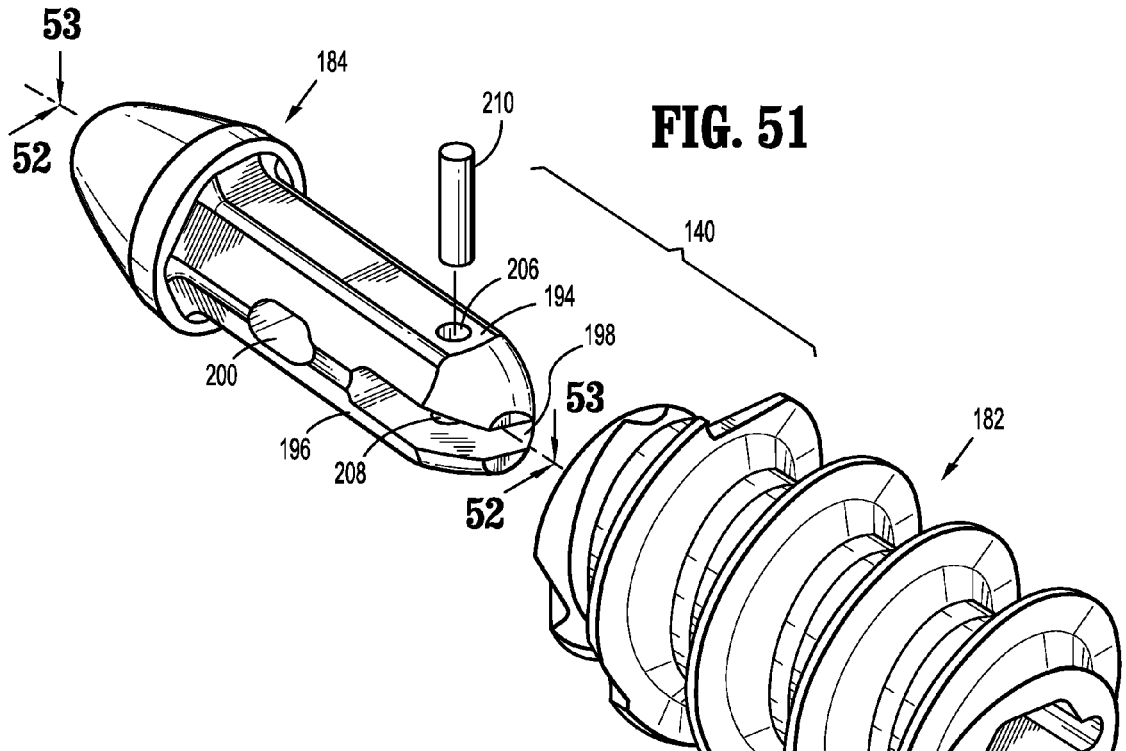
FIG. 51
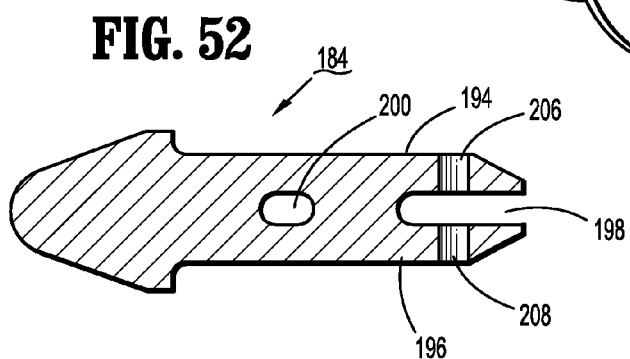
FIG. 52
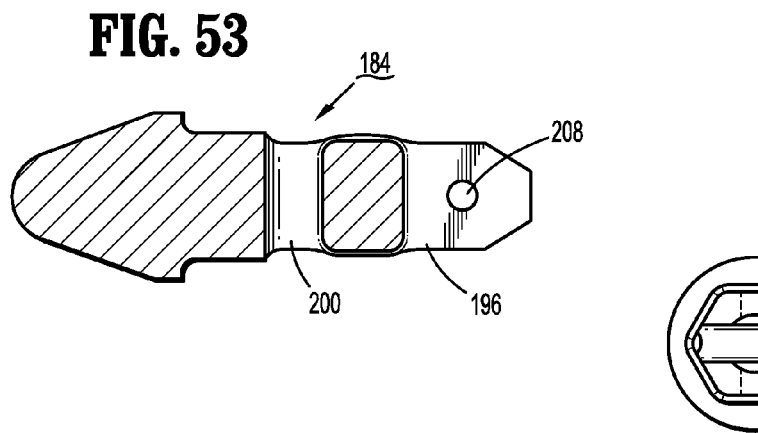
FIG. 53
FIG. 54

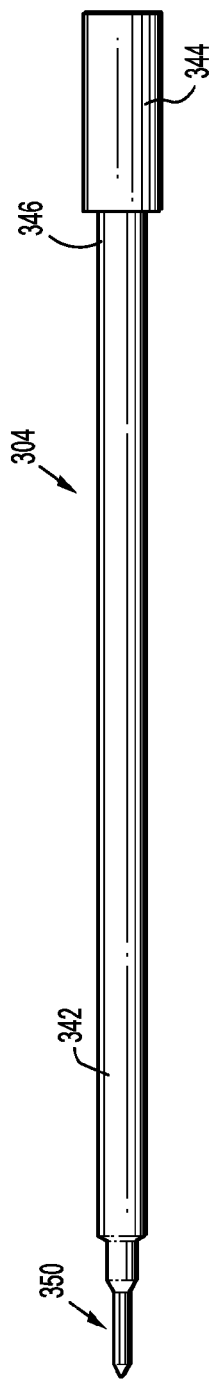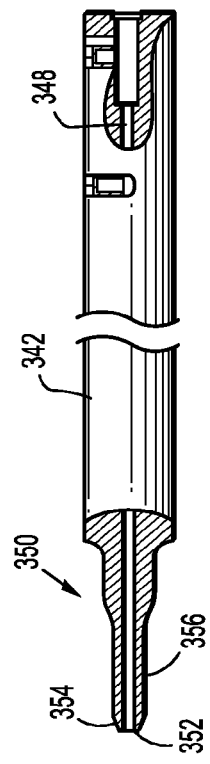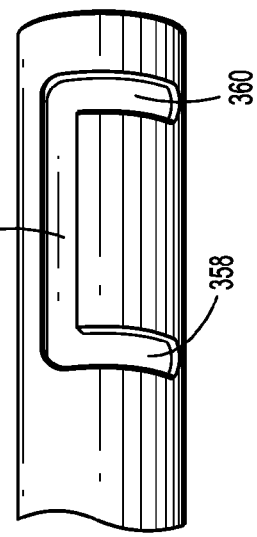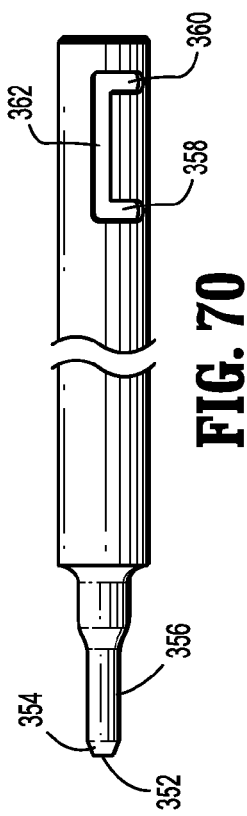
FIG. 68
FIG. 69
FIG. 70
FIG. 71

SUTURE ANCHORS

CROSS REFERENCE TO RELATED APPLICATIONS

This application claims the benefit of and priority to U.S. Provisional Patent Application No. 60/660,499, filed Mar. 10, 2005.

BACKGROUND

1. Technical Field

The technical field relates to tissue repair and, in particular, relates to cannulated and uncannulated suture anchors for securing tissue to bone.

2. Background of Related Art

Suture anchors are typically used to secure lengths of suture relative to various body parts. In one class of particular application, suture or bone anchors are used to position and secure a length of suture relative to bone. For example, suture anchors are used to secure portions of tissue adjacent a bone surface. A conventional method involves implanting a suture anchor into bone and using the suture attached to the suture anchor to secure tissue adjacent to the bone. This method finds particular application in various forms of reconstructive surgery.

In an alternative use of a suture anchor, the suture anchor and associated suture can be used to secure torn or damaged ligaments, relative to bone. In this method, typically, a longitudinal bore is drilled into bone and a suture anchor is positioned within the drilled bore. The suture anchor may be secured within the bore via a wedging, threading and/or use of adhesive. Once the suture anchor has been secured to a proper depth within the drilled bore in bone, an end of the suture may be secured to a ligament and the ligament drawn adjacent the bone thereby reattaching the ligament is to the bone.

While the described methods of utilizing suture anchors to secure tissue and/or ligaments to bone are known in the art, there exists a need for a multi-component suture anchor capable of adjusting the length and tension of the suture on associated tissue.

SUMMARY

Accordingly, in one preferred embodiment of the present disclosure, a suture anchor includes an outer sleeve having a longitudinal throughbore with leading and trailing ends and an insert positionable within the longitudinal throughbore of the outer sleeve. The insert defines at least one suture track for slidably supporting a suture whereby opposed free ends of the suture extend from the at least one suture track through the longitudinal throughbore to extend beyond the trailing end of the outer sleeve to be tensioned and secured relative to the tissue. The insert preferably includes a pair of suture tracks for supporting a pair of sutures. The suture tracks may incorporate channels formed in an outer surface of the insert. Alternatively, the suture tracks may include openings extending through the insert. The openings may be radially spaced in side by side relation or longitudinally spaced along the insert.

The insert may be operatively connected to the outer sleeve whereby rotation of the outer sleeve causes corresponding rotation of the insert. A preferred insert includes a shaft and a relatively enlarged leading tip. The shaft is receivable within the longitudinal throughbore of the outer sleeve. The leading tip has a dimension greater than a corresponding dimension of the longitudinal throughbore to be external of the outer sleeve. The leading tip may define a conical portion. Alternatively, the insert is entirely positioned within the longitudinal throughbore of the outer sleeve. In this embodiment, the outer sleeve has at least one longitudinal slot at a distal end thereof such that the insert is positionable within the throughbore and the slot.

The present disclosure also relates to a suture anchor system. A preferred suture anchor system includes a suture anchor having an outer sleeve with an external thread and an insert at least partially positioned within the outer sleeve, and an anchor driver adapted to install the suture anchor in tissue. The insert of the suture anchor has a pair of suture tracks for slidably supporting a pair of sutures whereby the sutures are looped relative to the suture tracks with respective suture end portions extending through the outer sleeve and out the trailing end thereof. The anchor driver includes a driver shaft and a driver tip. At least the driver shaft has a pair of longitudinal recesses defined in an outer surface thereof for reception of respective suture end portions extending from the outer sleeve. The driver tip is operatively engageable with the outer sleeve of the suture anchor whereby rotational movement of the anchor driver causes corresponding rotational movement of the outer sleeve and advancement of the suture anchor into the tissue.

The insert of the suture anchor includes a longitudinal bore extending therethrough for reception and passage of a guide wire. Similarly, the anchor driver may include a longitudinal bore therethrough for reception and passage of a guide wire.

The system may include a guide wire punch for facilitating entry of a guide wire into the tissue. The guide wire punch includes a punch shaft defining a longitudinal bore for reception and passage of a guide wire and an impactor cap mountable to the punch shaft. The impactor cap has an internal pin dimensioned to be received within the longitudinal bore of the punch shaft when the impactor cap is mounted to the punch shaft whereby advancement of the impactor cap onto the punch shaft causes the internal pin to engage and drive the guide wire into the tissue. The impactor cap may be tethered to the punch shaft with a tether line. In this embodiment, the impactor cap and the tether line are formed of a polymeric material.

BRIEF DESCRIPTION OF THE DRAWINGS

Various embodiments of the presently disclose cannulated suture anchor are described herein with reference to the drawings, wherein:

FIG. 1 is a perspective view of a cannulated suture anchor and associated suture anchor driver;

FIG. 2 is an enlarged area of detail of FIG. 1;

FIG. 14 is a perspective view partially shown in section of a cannula and a guide wire punch installing a guide wire in tissue;

FIG. 15 is a view similar to the view of FIG. 14 illustrating the guide wire punch removed leaving the guide wire extending through the cannula;

FIG. 16 is a perspective view of the suture anchor mounted to a suture driver and being advanced over the guide wire;

FIG. 17 is a perspective view, partially shown in section, of the suture driver and mounted suture anchor advanced within a cannula;

FIG. 18 is a view of the suture anchor and associated sutures installed through tissue and within bone;

FIG. 29 is a further perspective view of the suture anchor with parts separated;

FIG. 30 is a cross-sectional view of the suture retaining insert taken along line 30-30 of FIG. 29;

FIG. 31 is a cross-sectional view of the suture retaining insert taken along line 31-31 of FIG. 29;

FIG. 37 is a perspective view of a non-cannulated suture anchor in accordance with another embodiment of the present disclosure;

FIGS. 38-39 are perspective views with parts separated of the suture anchor of FIG. 37 illustrating the threaded outer member and the insert;

FIG. 43 is a perspective view illustrating the suture anchor being assembled with sutures;

FIG. 44 is a perspective view illustrating the suture anchor being positioned on an anchor driver;

FIG. 50-51 are perspective views with parts separated of the suture anchor of FIG. 49 illustrating the threaded outer member end of the insert;

FIG. 52 is a cross-sectional view of the insert taken along line 52-52 of FIG. 51;

FIG. 53 is a cross-sectional view of the insert taken along line 53-53 of FIG. 51;

FIG. 54 is an end view of the insert;

FIG. 68 is a side plan view of the guide wire punch of the suture anchor system of FIG. 62;

FIGS. 69-70 are side plan views in partial section of the guide wire punch;

FIG. 71 is an enlarged plan view of the proximal end portion of the punch shaft of the guide wire punch of FIG. 68;

DETAILED DESCRIPTION OF EMBODIMENTS

Figure 3:
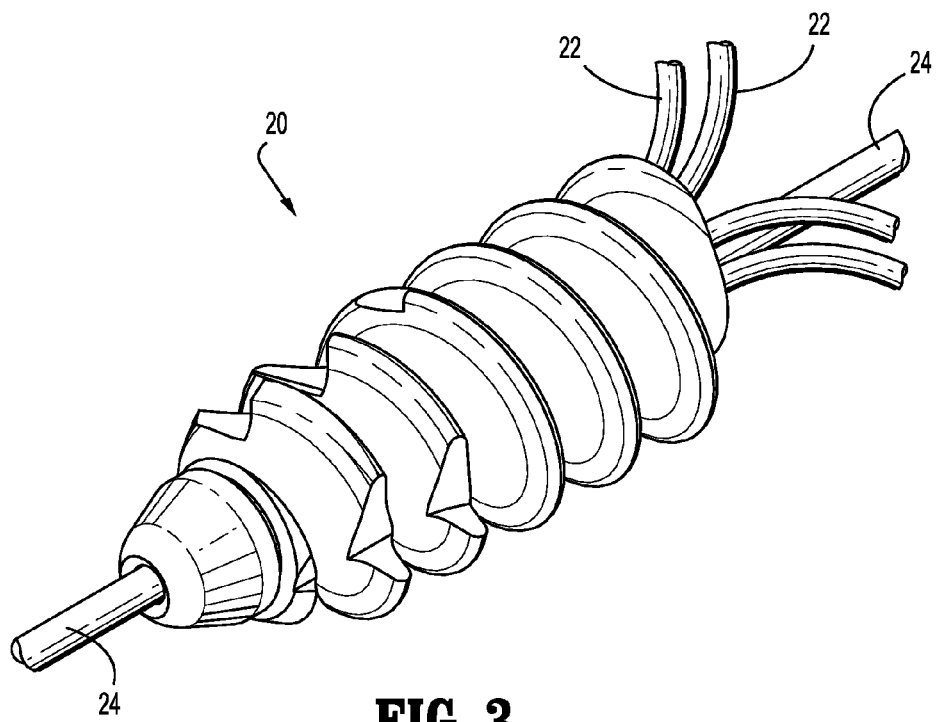
FIG. 3 is a perspective view of the cannulated suture anchor assembled with sutures and a guide wire.
Figure 4:
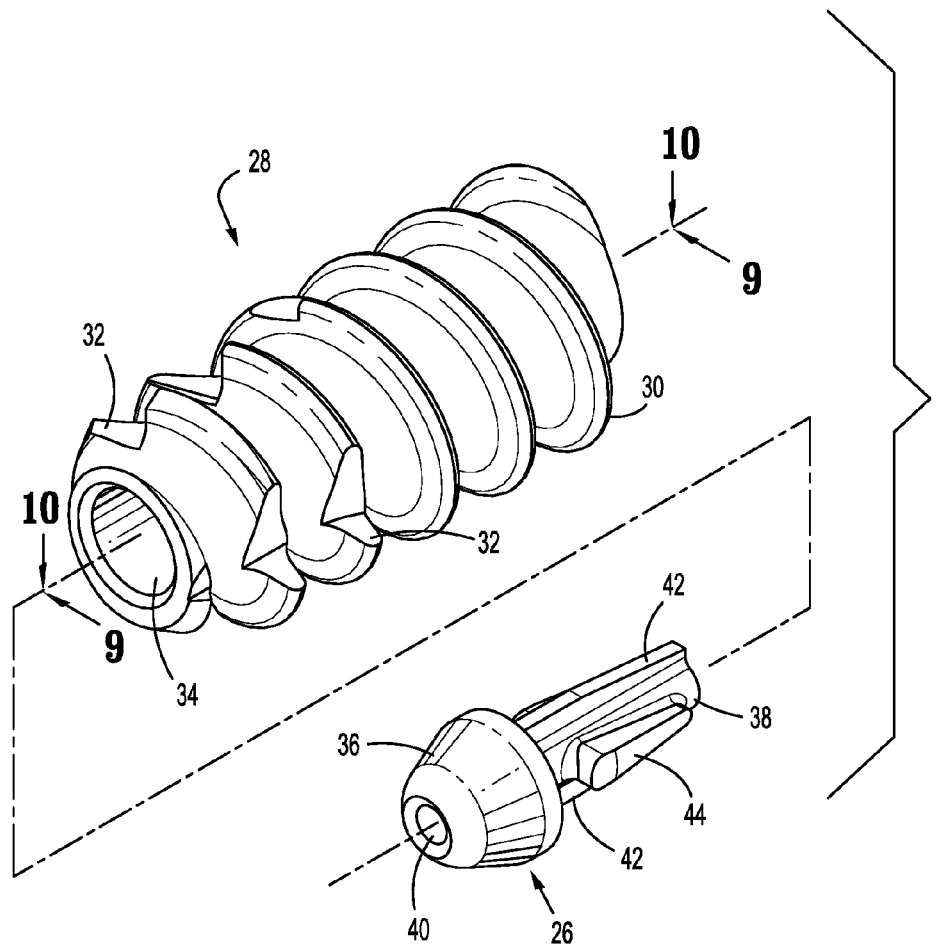
FIG. 4 is a perspective view of the cannulated suture anchor with parts separated illustrated the threaded outer member and the insert.
Figure 5:
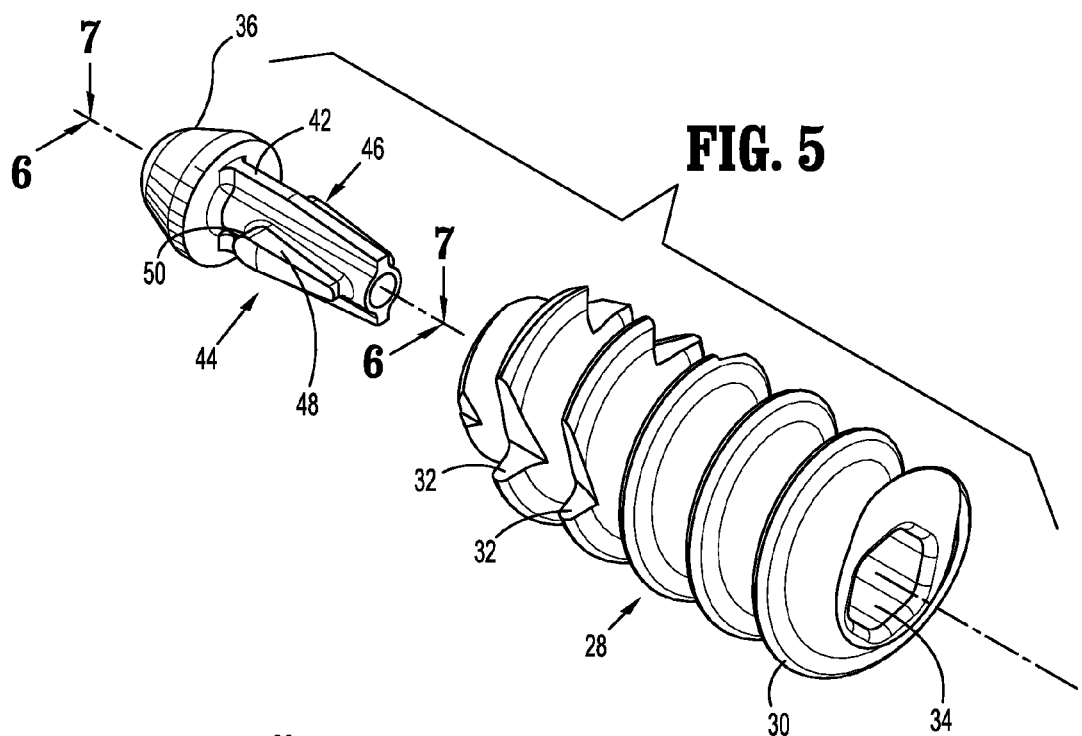
FIG. 5 is another perspective view of the cannulated suture anchor.
Figure 6:
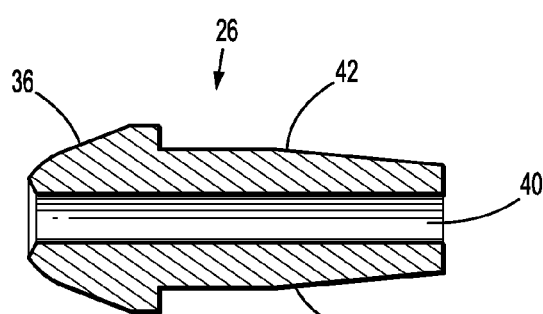
FIG. 6 is a cross-sectional view taken along the line 6-6 of FIG. 5.
Figure 7:
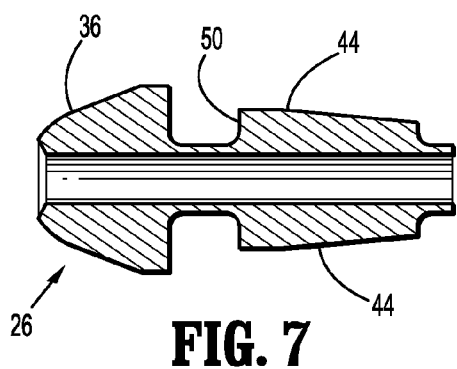
FIG. 7 is a cross-sectional view taken along the line 7-7 of FIG. 5.
Figure 8:
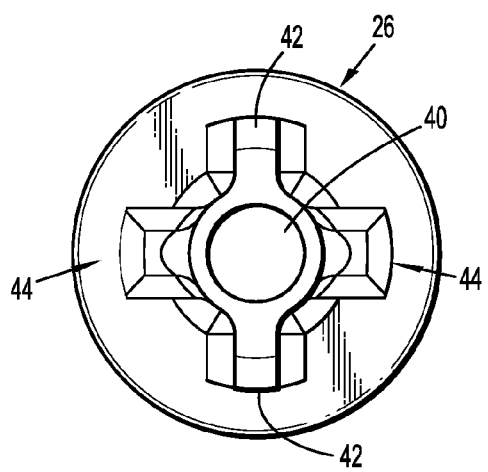
FIG. 8 is an end view of the insert of the cannulated suture anchor.

A cannulated suture anchor is disclosed herein along with a suture anchor driver in order to install the cannulated suture anchor over a guide wire and into a bore predrilled in bone. Thereafter, sutures can be attached to tissue and adjusted through the suture anchor so as to cinch the tissue to the proper tension relative to the adjacent bone.

Referring now to FIG. 1, there is disclosed a suture anchor system 10 including a suture anchor driver 12. Suture anchor driver 12 is substantially similar to that disclosed in U.S. provisional patent application Ser. No. 60/564,249, filed on Apr. 21, 2004 and entitled HERCULON ANCHOR AND APPLIER, except that the presently disclosed suture anchor driver 12 includes a throughbore extending completely through the suture anchor driver 12 in order to advance suture anchor driver 12 over a guide wire. Suture anchor driver 12 generally includes a handle 14 having an elongate drive shaft 16 extending distally from handle 14. A suture anchor mount 18 extends distally from drive shaft 16 in order to support a cannulated suture anchor 20 for insertion into a bore in bone.

Referring for the moment to FIG. 2, cannulated suture anchor 20 is mounted on a distal end of anchor mount 18 and is configured to receive a suture 22 partially through cannulated suture anchor 20. Proximal tension on suture 22 retains suture anchor 20 on anchor mount 18.

Referring now to FIG. 3, as shown, a guide wire 24 extends completely through cannulated suture anchor 20. Additionally, a plurality of sutures 22 enter and exit cannulated suture anchor 20.

Cannulated suture anchor 20 generally includes an insert 26 and a threaded outer member 28. Cannulated suture anchor 20 is preferably formed of a bio-compatible material such as for example, stainless steel, titanium, etc. Additionally, cannulated suture anchor 20 may be formed of a bio-absorbable or re-sorbable material.

Threaded outer member 28 includes a plurality of circumferential threads 30 along the length of threaded outer member 28. At a distal most end of threaded outer member 28, threads 30 are interrupted by cutting edges 32 which facilitates cutting into a bore in bone as cannulated suture anchor 20 in rotated into the bone. It should be noted that threads 30 are generally of constant pitch and relatively constant diameter along the length of threaded outer member 28. Threaded outer member 28 also includes a longitudinal throughbore 34 extending completely through hollow bore body portion 28 for receipt of insert 26.

Referring now to FIGS. 4-8, insert 26 includes a conical nose cap 36 and a proximal portion or shaft 38 which extends proximally from the nose cap 36. A bore 40 extends completely through insert 26 for receipt of guide wire 24. Proximal portion or shaft 38 includes a pair of opposed alignment fins 42 which are configured to engage corresponding slots 43 (FIG. 9) in threaded outer member 28. In order to support sutures 22, proximal portion 38 is also provided with a pair of opposed suture guides 44 which are configured to allow suture 22 to enter cannulated suture anchor 20 and exit cannulated suture anchor 20 at a proximal portion thereof. This enables one end of the suture to be attached to tissue and, when installed in bone, the opposed ends of suture 22 may be tensioned so as to draw the tissue adjacent or within a bore in bone. Suture guides 44 generally include a pair of opposed suture tracks 46 which each include a pair of sides 48 and an arcuate distal end 50. Suture 22 extends along suture tracks 46 by lying against sides 48 and curving around arcuate distal end 50.

Suture tracks 46 may be parallel, preferably, suture track sides 48 taper from a greatest distance at the distal end to a smaller distance at a proximal end to facilitate free movement of the suture within cannulated suture anchor 20. It should be noted that the maximum diameter dimension of proximal portion 38 is at all times less than the maximum outer diameter of nose cap 36.

Figure 9:
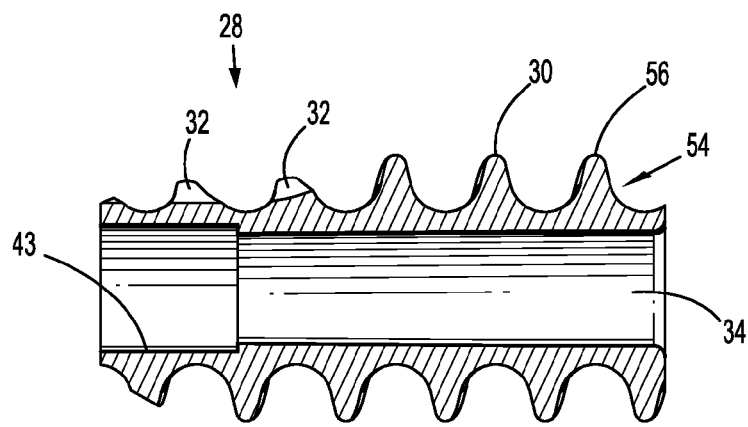
FIGS. 9-10 are side cross-sectional views of the threaded outer member of the cannulated suture anchor.
Figure 10:
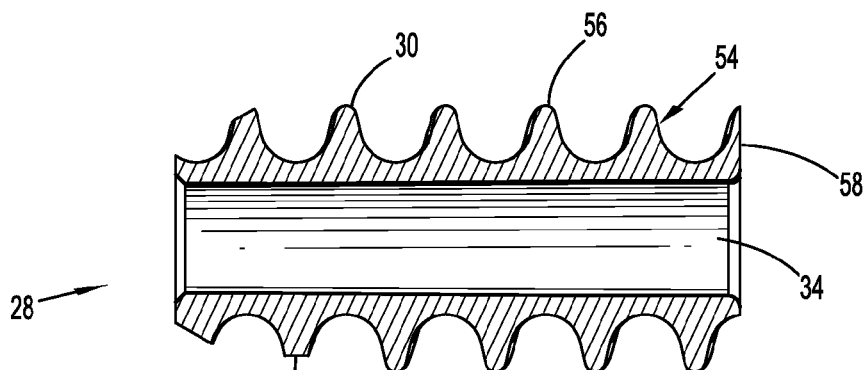
Figure 11:
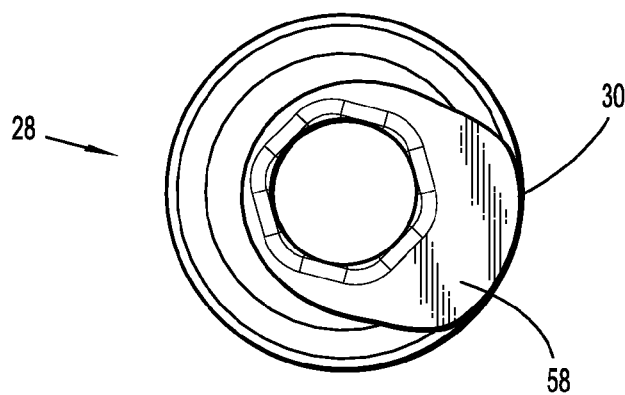
FIG. 11 is an end view of the threaded outer member of the cannulated suture anchor.

Referring now to FIGS. 9-11, proximal threads 54 of threads 30 are preferably provided with curved atraumatic surfaces 56 to prevent excessive cutting of threads 30 within a bore in bone, which would tend to weaken the securement of cannulated suture anchor 20 within a predrilled bore in bone. As noted above, while threads 30 are generally of constant diameter throughout the length of threaded outer member 28, it should be noted that the interrupted cutting edges 32 would tend to reduce the diameter of any threads 30 formed therein. As shown in FIGS. 10 and 11, a proximal most end 58 is generally sectioned in half at the proximal end of threaded outer member 28.

Figure 12:
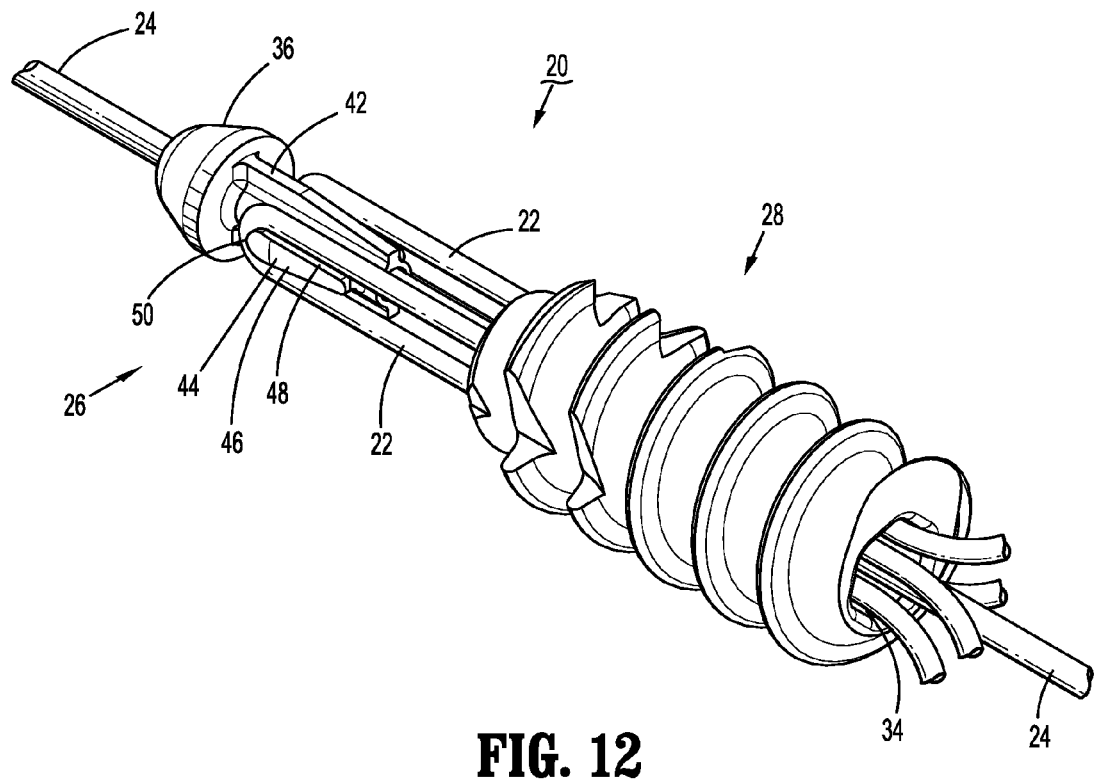
FIG. 12 is a perspective view of the cannulated suture anchor with parts separated and assembled with sutures and a guide wire.
Figure 13:
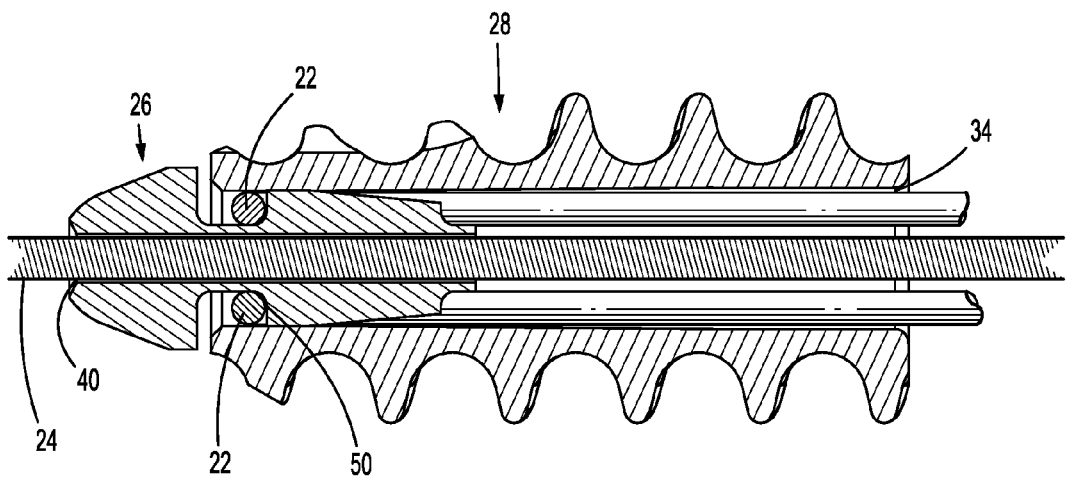
FIG. 13 is a cross-sectional view of the cannulated suture anchor with sutures and guide wire.

Referring now to FIGS. 12-18, the assembly and operation of use of cannulated suture anchor 20 to secure tissue within or adjacent a bore in a bone, by means of suture 22 extending therethrough, will now be described. With particular reference to FIGS. 12-13, the assembly of cannulated suture anchor 20 will now be described. Initially, a pair of sutures 22 are threaded through threaded outer member 28 and extend along sides 48 of suture tracks 46 around arcuate distal end 50 of suture track 46 and back proximally around opposing sides 48 of suture tracks 46. This free end of the suture is then again passed through bore 34 in threaded outer member 28 to leave two ends of the same suture 22 extending around suture guides 44 with the free ends of the suture extending out of the proximal end of bore 34.

For illustrative purposes, guide wire 24 is shown extending through bore 34 in threaded outer member 28 and bore 40 in insert 26. In this manner, cannulated suture anchor 20 can be advanced along with suture 22 and into a bore in bone using guide wire 24 as a guide into the bore in bone.

In operation, suture anchor system 10 can be used to install cannulated suture anchor 20 into a bone B having over lying tissue T. Sutures 22 would be then used to secure tissue T to bone B, as shown. In an alternative preferred embodiment, not illustrated, cannulated suture anchor 22 can be used to be installed in a bore in bone and sutures 22 used to attach a ligament into the bore in bone.

Referring to FIG. 14, initially, a cannula 60 is provided included a housing 62 and a sleeve 64 extending distally from body portion 62. Cannula 60 has a throughbore 66 extending completely therethrough for receipt of the various instruments.

In order to position or initially install guide wire 22 through tissue T and into bone B there is provided a guide wire punch 68 having a t-shaped handle 70 and an elongate shaft 72 extending distally from handle 70. A conical punch tip 74 is formed on the distal end of elongate shaft 72 to advance guide wire punch 68 through tissue and into bone. Guide wire punch 68 also has a guide wire throughbore 76 extending completely therethrough. In use, guide wire punch 68 having a guide wire 22 extending therethrough is advanced through bore 66 of cannula 60 and forced through tissue T and bone B such that a distal end 78 of guide wire 22 is driven into bone B. Once distal end 78 of guide wire 22 has been inserted into bone B, guide wire punch 68 can be removed from cannula 60 leaving guide wire 22 extending through cannula 60 as shown in FIG. 15.

Referring now to FIG. 16, guide wire 22 is then threaded through suture anchor system 10 such that suture anchor system 10 including cannulated suture anchor 20 can be advanced over guide wire 22 towards tissue T. As shown in FIG. 17, driver 12 can be used to force suture anchor 20 through tissue T and adjacent bone B. Thereafter, driver 12 is rotated such that cannulated suture anchor 20 is driven into bone B. As noted hereinabove, cannulated suture anchor 20 includes interrupted cutting edges 32 which facilitate cutting a bore in bone B as cannulated suture anchor 20 is rotated therein.

Once cannulated suture anchor 20 has been installed in bone B, guide wire 24 can be removed through suture anchor system 10. Suture anchor driver 12 can then be disengaged from cannulated suture anchor 20. Preferably, this is accomplished by slight release on the tension of sutures 22 which held cannulated suture anchor 20 on anchor mount 18. Thereafter, driver 12 can be completely removed through cannula 60 and cannula 60 can be removed through the tissue leaving cannulated suture anchor 20 installed in the bone with sutures 22 extending out a proximal end of cannulated suture anchor 20 and through tissue, as shown in FIG. 18. At this point, a further step would be to knot sutures 22 such that tissue T is secured to bone B. Alternatively, one free end of each individual suture could be secured adjacent tissue T and the opposed free end of suture 22 pulled in the direction of arrows A to draw the opposed ends of suture in the direction of arrows B as the suture 22 is pulled within cannulated suture anchor 20 and around suture guides 44.

Notably, in an alternative use not shown, cannulated suture anchor 20 would be installed in a bore pre-drilled in bone. Once installed, one free end of each suture would be attached to an end of a ligament and as the opposed free ends of the suture are tensioned to draw suture through cannulated suture anchor 20 and around suture guides 44, the ligament would be drawn into the bore in bone B to thereby secure the ligament within the bore or bone B. A further additional advantage of cannulated suture anchor 20 is that by tensioning the free end of the suture attached to a ligament, the proper tension of the ligament with the bore in bone B may be achieved.

Figure 19:
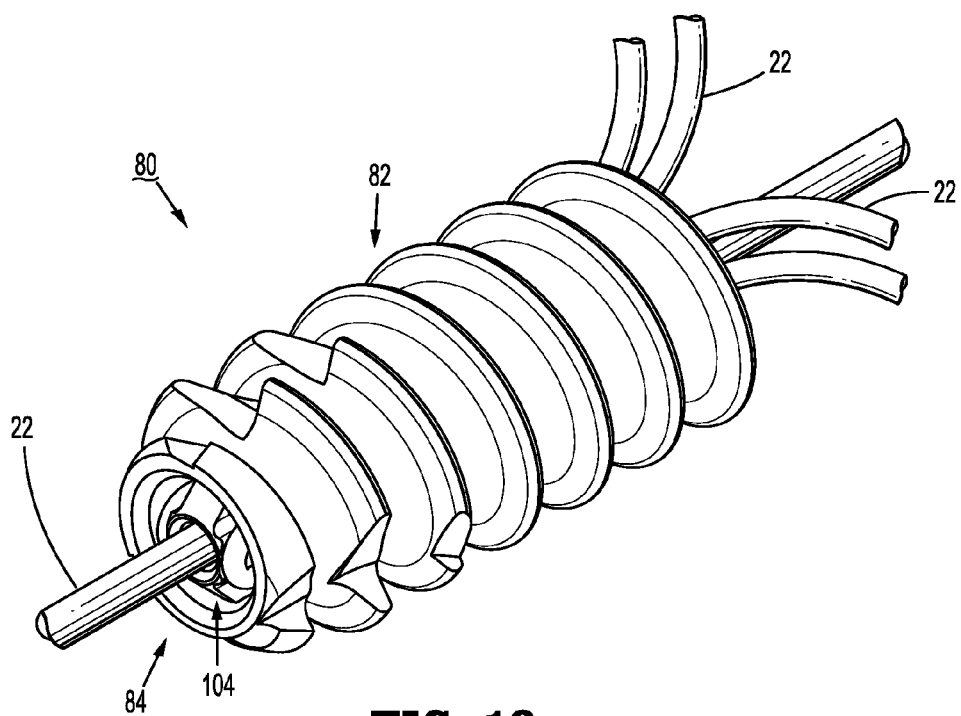
FIG. 19 is a perspective view of an alternate embodiment of the cannulated suture anchor.
Figure 20:
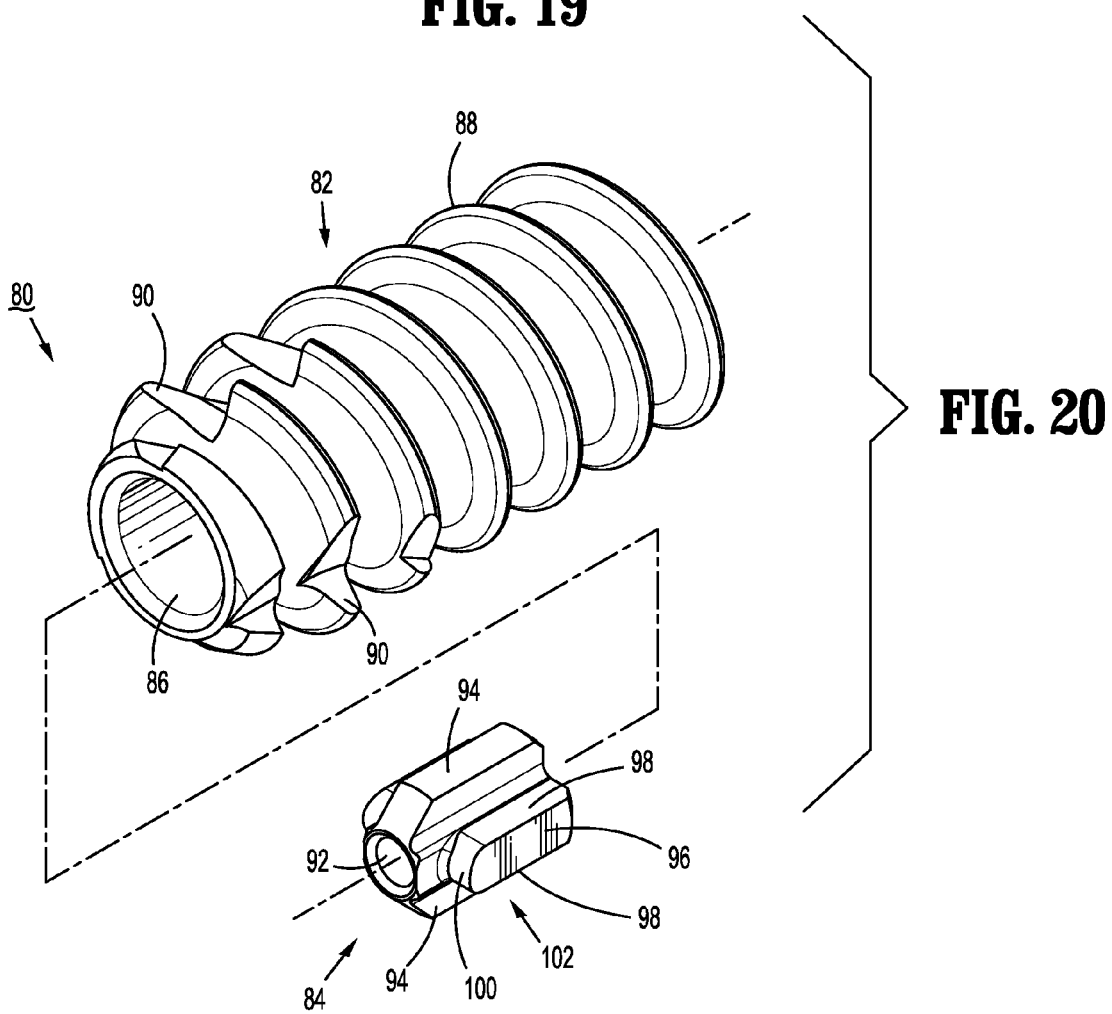
FIG. 20 is a perspective view of the cannulated suture anchor of FIG. 19 with parts separated.

Referring now to FIGS. 19-26, and initially to FIGS. 19 and 20, there is disclosed an alternate embodiment of a cannulated suture anchor which is particularly suited for insertion in a predrilled bore within bone. Cannulated suture anchor 80 generally includes a threaded outer member 82 and an insert 84, insertable within a throughbore 86 formed in threaded outer member 82. Throughbore 86 extends completely through threaded outer member 82 in a manner similar to that of cannulated suture anchor 20 described hereinabove. Threaded outer member 82 includes continuous threads 88 formed around threaded outer member 82. Threads 88 are generally of constant diameter and pitch. A plurality of cutting edges 90 are formed at a distal section of threads 88 to facilitate cutting into a bore formed in bone. It should be noted that when a bore is formed in bone for use with cannulated suture anchors disclosed herein, the bore is preferably of a slightly subdiameter to the threads such that interrupted cutting edges 90 cut a threaded surface into the bore of the bone to secure the cannulated suture anchor therein.

As shown in FIG. 19, assembled suture anchor 80 is configured to receive a guide wire 24 completely therethrough. Additionally, as with the prior embodiment, pairs of sutures 22 can extend into cannulated suture anchor 80 and out the proximal end in the same manner described hereinabove with cannulated suture anchor 10.

Referring to FIGS. 20-24, insert 84 is provided without an enlarged conical tip as was provided with insert 26 described hereinabove. The lack of a conical tip is not deemed disadvantageous in this particular embodiment, as it is designed to go into a relatively large diameter bore formed in bone and need not avail itself of the guiding function of the conical tip of insert 26 described hereinabove. Insert 84, includes alignment fins 94 formed on opposed sides of insert 84, as well as a pair of suture guides 96, again formed on opposed sides of insert 84.

Suture guides 96 differ from those previously described in that sides 98 of suture guides 96 are generally parallel to each other. An arcuate distal end 100 is provided on suture guide 96 such that sides 98 and arcuate distal end 100 define a suture track 102 about which sutures 22 can be positioned or looped. Insert 84 also includes a throughbore 92 formed completely therethrough for receipt of guide wire 24. As best seen in FIG. 19, a distal end 104 of insert 84, when assembled with threaded outer member 82, is recessed within a distal end 106 of threaded outer member 82.

Figure 21:
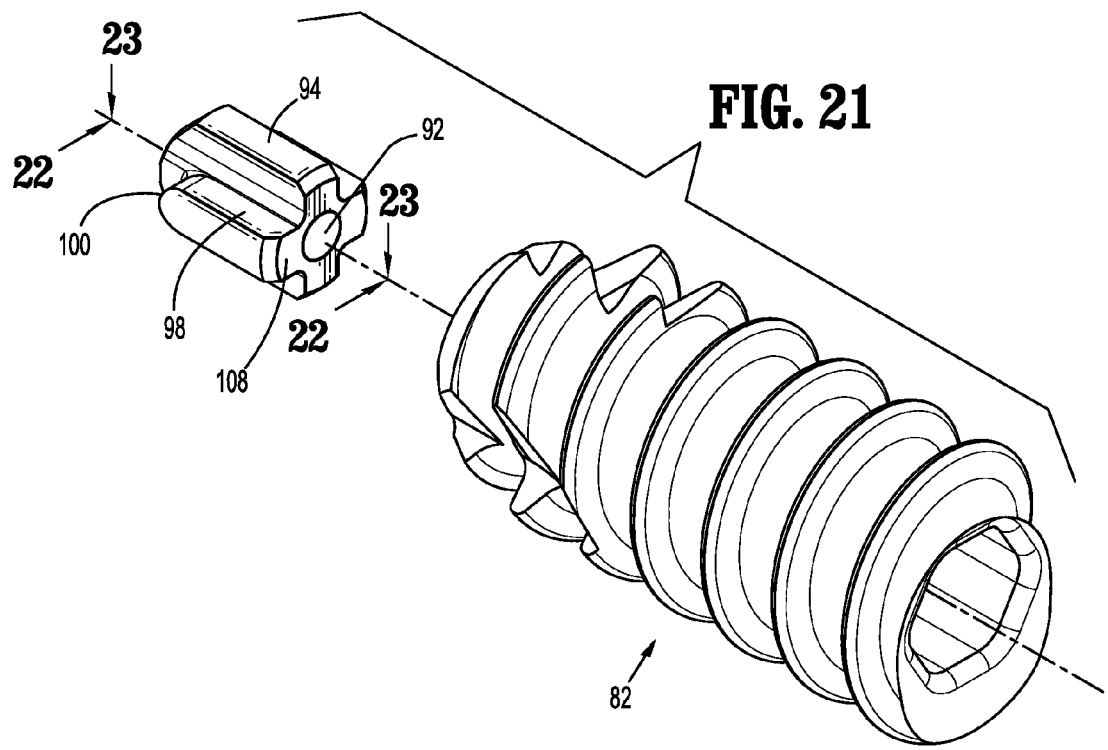
FIG. 21 is another perspective view of the cannulated suture anchor with parts separated.
Figure 22:
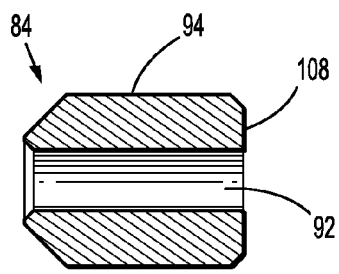
FIG. 22 is a cross-sectional view of the insert of the suture anchor taken along line 22-22 of FIG. 21.
Figure 23:
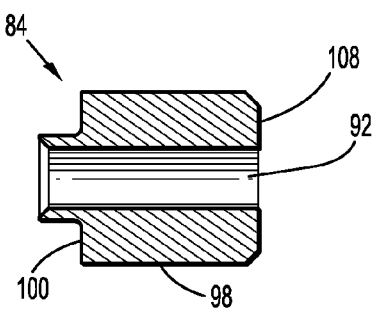
FIG. 23 is a cross-sectional view of the insert of the suture anchor taken along line 23-23 of FIG. 21.
Figure 24:
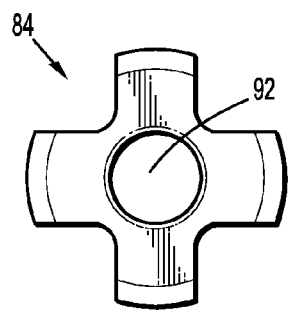
FIG. 24 is an end of view of the insert.

As best seen in FIGS. 21-23, a proximal end 108 of insert 84 is flush. This is in contrast to a proximal end of the prior insert where the proximal ends of the suture guide 44 do not extend all the way to the proximal end of insert 26.

Figure 25:
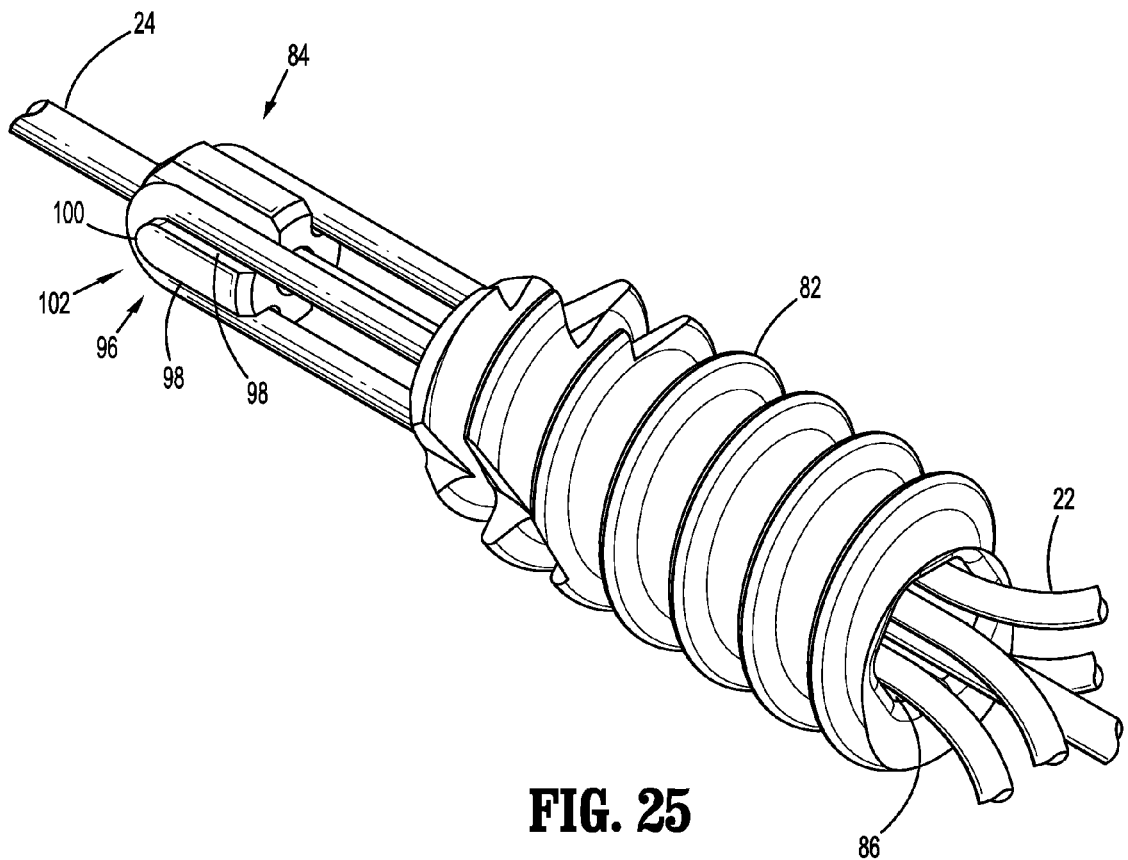
FIG. 25 is a perspective view of the cannulated suture anchor, with parts separated, assembled with associated sutures and guide wire.
Figure 26:
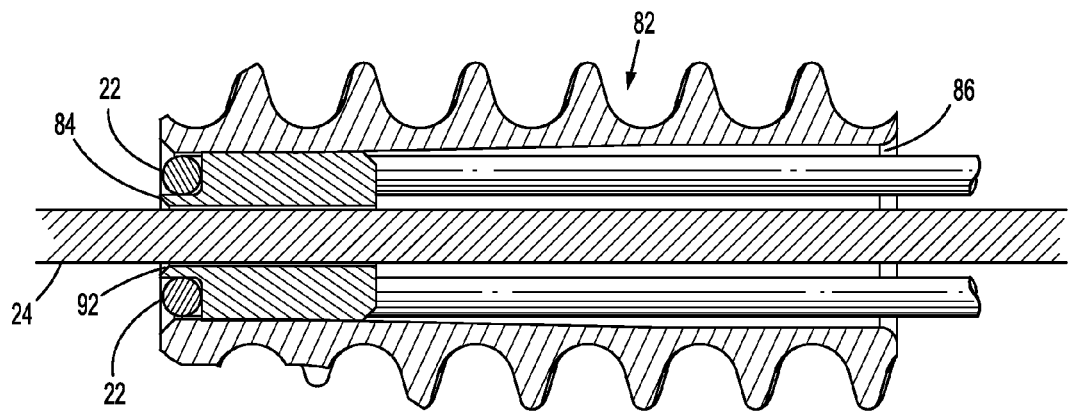
FIG. 26 is a cross-sectional view of the assembled suture anchor including sutures and guide wire.
Figure 27:
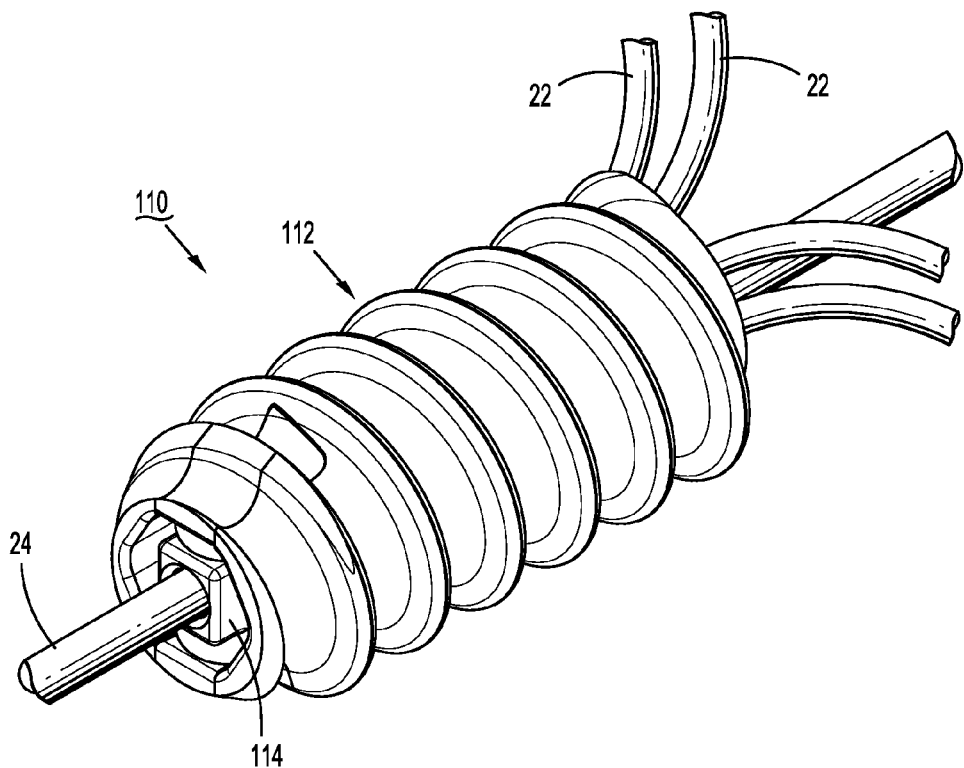
FIG. 27 is a perspective view of a further alternate embodiment of a cannulated suture anchor.
Figure 28:
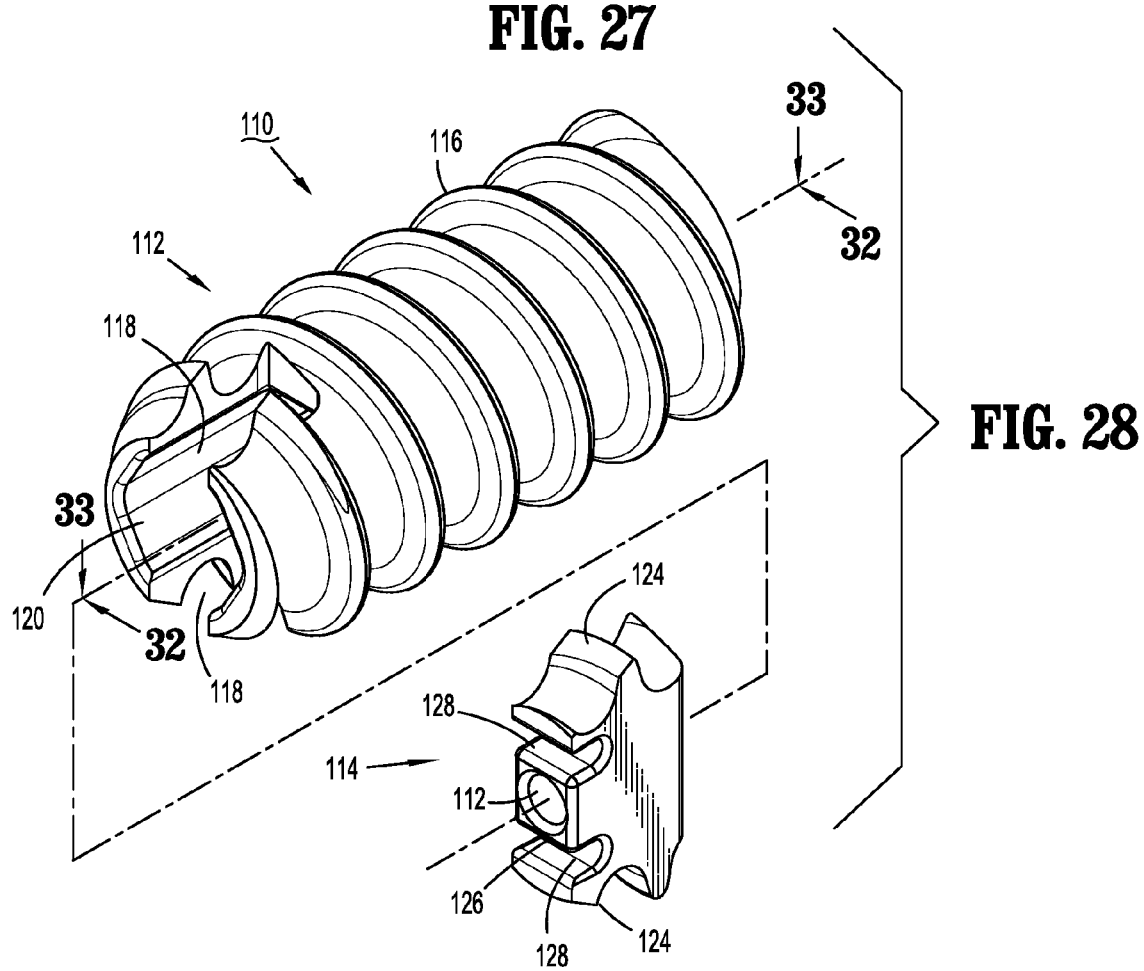
FIG. 28 is a perspective view of the suture anchor of FIG. 27 with parts separated.

Referring to FIGS. 25-26, it can be seen that when cannulated suture anchor 80 is assembled, sutures 22 extend through bore 86 in threaded outer member 82. Sutures 22 are looped about suture guides 96 such that one portion of suture 22 extends along one side 98 of suture guide 96 and continues around arcuate distal end 100 to return up an opposed side 98 of suture guide 96. As noted above, sides 98 and arcuate distal end 100 define a suture track 102 formed in suture guides 96.

As best seen in FIG. 26, bore 86 of threaded outer member 82 and bore 92 of insert 84 form a continuous throughbore for receipt of guide wire 24. While not specifically shown, in use, a bore in bone would be drilled to a diameter slightly less than the outer diameter of threads 88 and guide wire 24 inserted into the bore formed in bone. Thereafter, utilizing a driver similar to driver 12 described hereinabove, cannulated suture anchor 80 would be advanced over guide wire 24 and into the bore formed in bone. Cannulated suture anchor 80 is inserted into the bone by rotating driver 12 in the manner described hereinabove with suture anchor assembly 10. Once cannulated suture anchor 80 has been positioned at the proper depth within a bore formed in bone, proximal ends of pairs of sutures 22 can be attached to a ligament and the opposed ends of suture 22 pulled or tensioned to draw the ligament into the bore in bone. Thereafter, the free ends of the suture would be tied off or tightened, or otherwise fixed relative to suture anchor 80 to secure the ligament within a bore formed in bone.

It should be noted that in all disclosed embodiments disclosed herein, the dimensional differences between the respective suture tracks and the internal diameter of the bore formed in the threaded outer member allow free movement of the suture through the threaded outer member and around the suture tracks, so as to draw tissue towards the suture anchor by tensioning opposed ends of the suture 22.

Referring now to FIGS. 27-36, there is disclosed a further alternate embodiment of a cannulated suture anchor 110 which, similar to cannulated suture anchor 80, is particularly configured for use within a predrilled bore formed in bone.

Cannulated suture anchor 110 generally includes a threaded outer member 112 and an insert 114 positionable within threaded outer member 112.

Threaded outer member 112 includes threads 116 formed about an outer surface thereof. As with prior embodiments, threads 116 are preferably of a constant diameter and pitch. A pair of cut-outs or slots 118 is formed at a distal end of threaded outer member 112 to receive insert 114. Threaded outer member 112 includes a throughbore 120 which extends completely through threaded outer member 112 for receipt of guide wire 24 and sutures 22.

Specifically referring to FIGS. 28-31, insert 114 includes a throughbore 122 for receipt of guide wire 24 therethrough. Unlike prior embodiments, insert 114 does not include any alignment tabs formed thereon. However, insert 114 is substantially the same diameter or width as threaded outer member 112. Insert 114 includes partial threads 124 formed on sides of insert 114. When insert 114 is inserted into slots 118 of threaded outer member 112, threads 124 of insert 114 along with threads 116 of threaded outer member 112 forms a continuous threaded surface. Insert 114 also includes a distally extending projection 126, through which insert bore 122 extends. The areas existing between distally extending projection 126 and threads 124, define a pair of opposed suture tracks 128 about which sutures 22 may be positioned.

Figure 32:
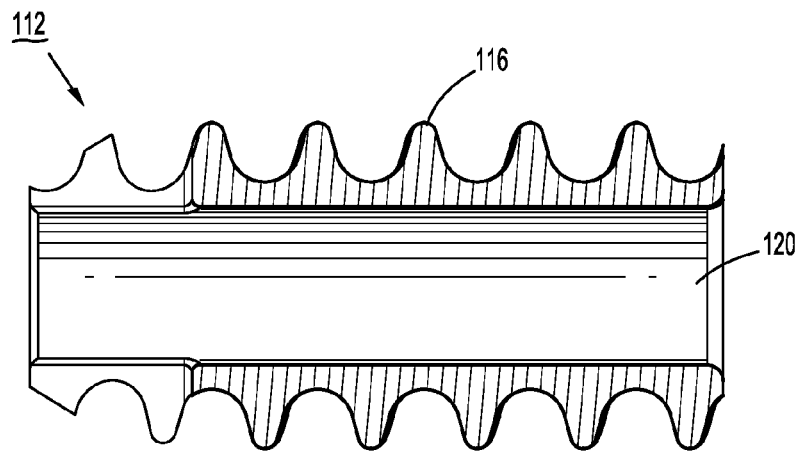
FIG. 32 is a cross-sectional view of the threaded outer member taken along line 32-32 of FIG. 28.
Figure 33:
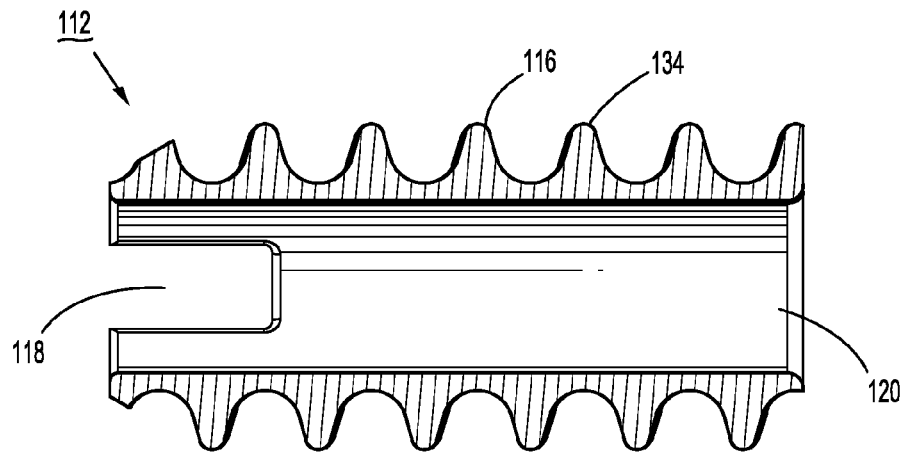
FIG. 33 is a cross-sectional view of the threaded outer member taken along line 33-33 of FIG. 28.
Figure 34:
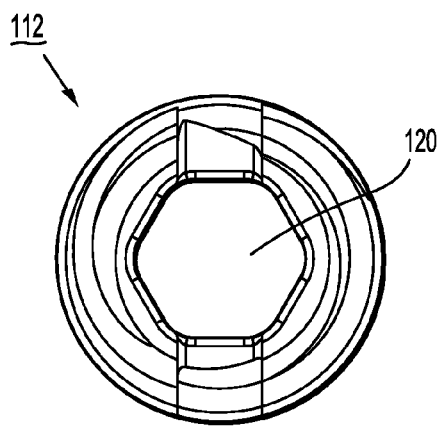
FIG. 34 is an end view of the threaded outer member.

Similar to cannulated suture anchor 80, a distal end 130 of insert 114 is slightly recessed within throughbore 120 relative to a distal end 132 of threaded outer member 112 when assembled. Referring to FIGS. 32-34, as noted above, threaded outer member 112 includes a throughbore 120 which is of substantially constant diameter. Threads 116 are interrupted at a distal end of threaded outer member 112 by slots 118. These interruptions are not provided for the purpose of forming cutting edges as with prior embodiments, but to receive insert 114 such that threads 124 of insert 114 form a continuous outer threaded surface of cannulated suture anchor 110. As with prior embodiments, the outer edges 134 of threads 124 are preferably atraumatic or rounded such that there is minimal cutting into bone as cannulated suture anchor 110 is threaded into bone.

Figure 35:
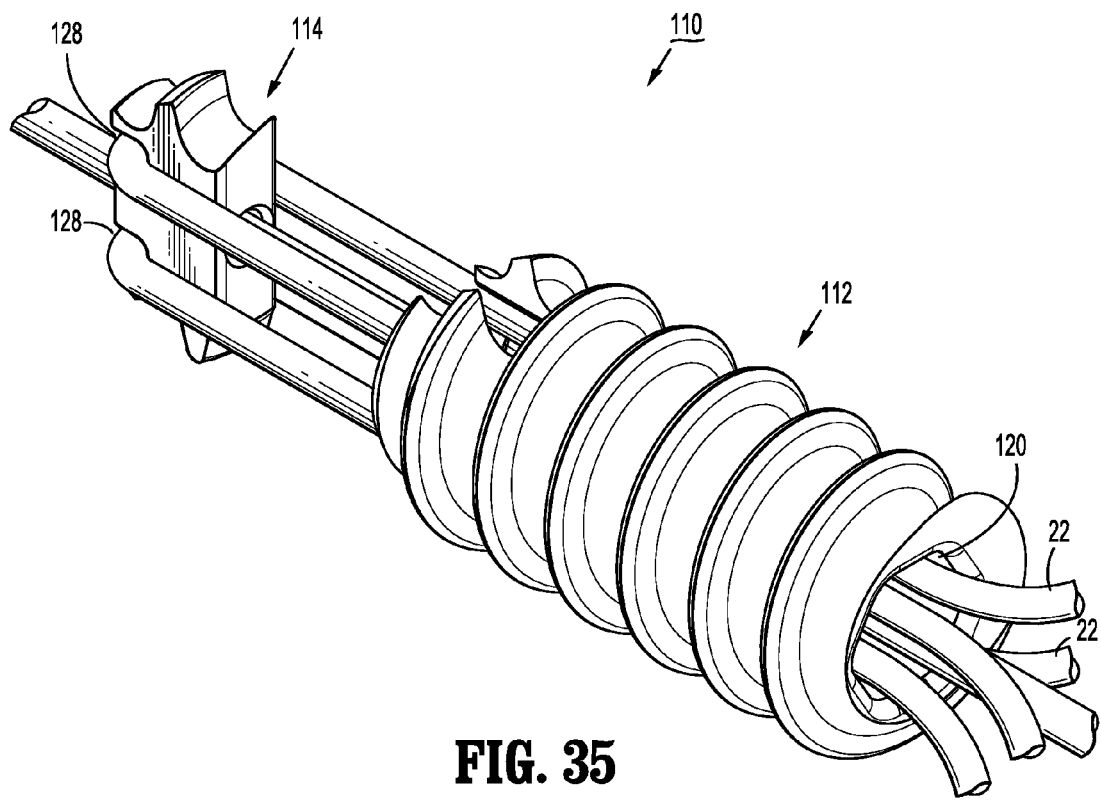
FIG. 35 is a perspective view of the suture anchor with parts separated including associated sutures and guide wire.
Figure 36:
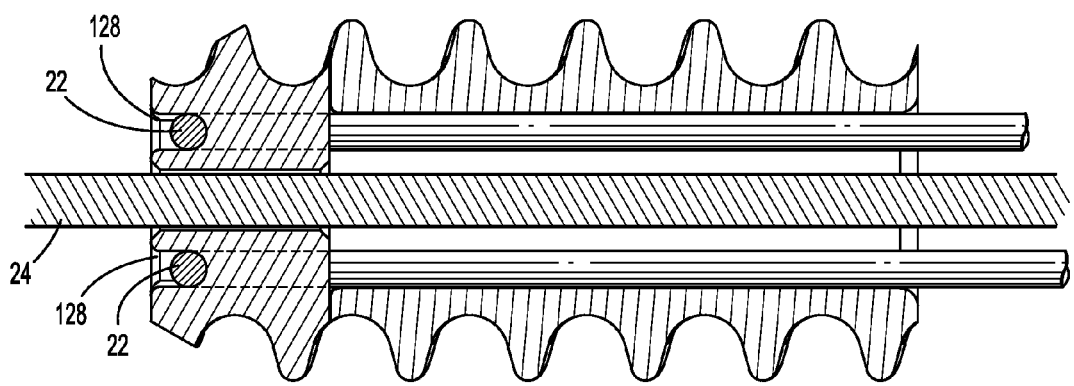
FIG. 36 is a cross-sectional view of the assembled suture anchor including associated sutures and guide wire.
Figure 39:
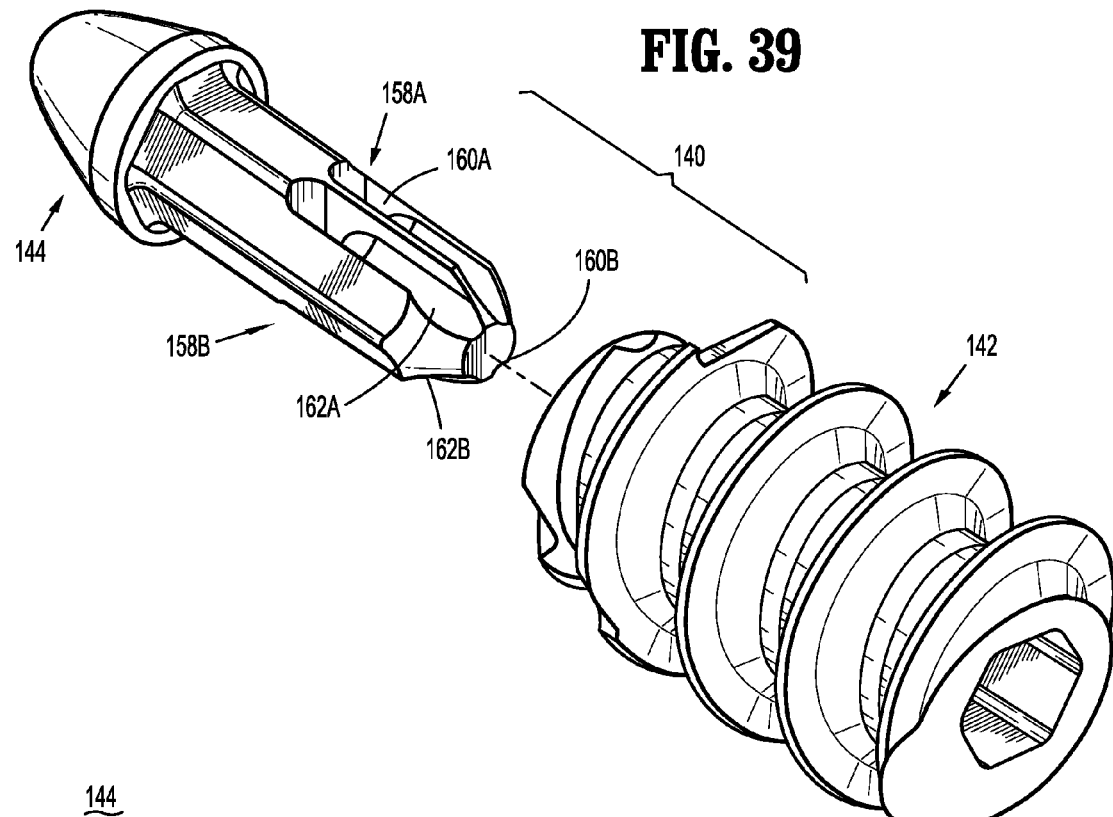
Figure 40:
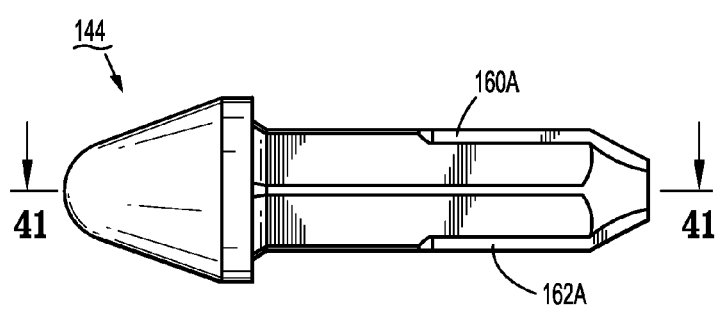
FIG. 40 is a side view of the insert of the suture anchor.

Referring now to FIGS. 35-36, cannulated suture anchor 110 is assembled in substantially a similar manner to cannulated suture anchor 80 described hereinabove. Specifically, sutures 22 are inserted through a bore 120 in threaded outer member 112 and looped about suture tracks 128 formed in insert 114. The free ends of suture 22 are then threaded back out through throughbore 120 such that both free ends of each suture extend proximally from throughbore 120. Once the sutures 22 have been properly positioned on insert 114, insert 114 is assembled to threaded outer member 112 by positioning the insert from a distal location within slots 118.

As specifically shown in FIG. 36, cannulated suture anchor 110, similar to cannular suture anchors described hereinabove, is configured to be advanced over a guide wire 24. It should be noted that the dimensional differences between the areas defined by suture tracks 128 and the inner diameter of throughbore 120 are sufficient such that the sutures may freely slide within throughbore 120 and about suture tracks 128. In use, cannulated suture anchor 110 is used in a substantially similar manner to that described hereinabove with respect to cannulated suture anchor 80.

Referring to FIGS. 37-48 and initially to FIGS. 37-38, there is disclosed a two-part, non-cannulated suture anchor 140 which generally includes a threaded outer member 142 and an insert 144 positionable within threaded outer member 142. Threaded outer member 142 includes a continuous outer thread 146 having interrupted cutting edges 148 at a distal end thereof. Threads 146 are generally of constant pitch throughout. Threaded outer member 142 additionally includes a hexagonal bore 150 for receipt of insert 144.

Insert 144 is provided to receive a pair of sutures and generally includes a conical tip 152 having a shaft 154 extending proximally from conical tip 152. A proximal end of shaft 154 is preferably has a tapered end 156. Insert 144 is provided with a pair of suture tracks 158A and 158B for receipt of a suture therearound. Suture tracks are provided such that a suture is disposed in the tracks can be tensioned or moved within suture anchor 140 in order to draw tissue adjacent bone after suture anchor 140 is installed in the bone.

Referring now to FIGS. 39-42, suture track 158A is defined by an opposed pair of longitudinal slots 160A and 160B formed in shaft 154. Similarly, suture track 158B is defined by longitudinal slots 162A and 162B formed in shaft 154. It should be noted that slots 160A and B are preferably parallel to each other and slots 162A and B are preferably parallel to each other. It should be further noted that slots 160A and B are longitudinally parallel to slots 162A and B.

Figure 41:
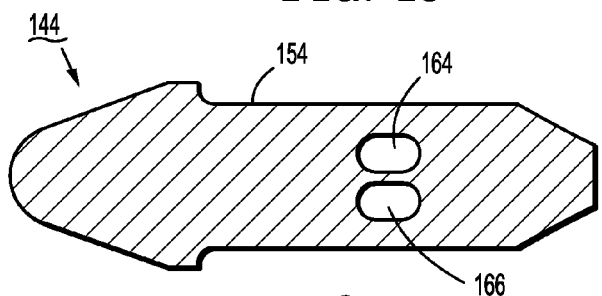
FIG. 41 is a cross-sectional view taken along the line 41-41 of FIG. 40.
Figure 42:
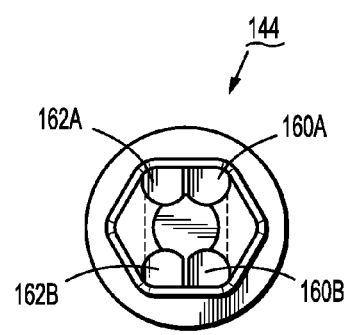
FIG. 42 is an end view of the non-cannulated suture anchor.
Figure 45:
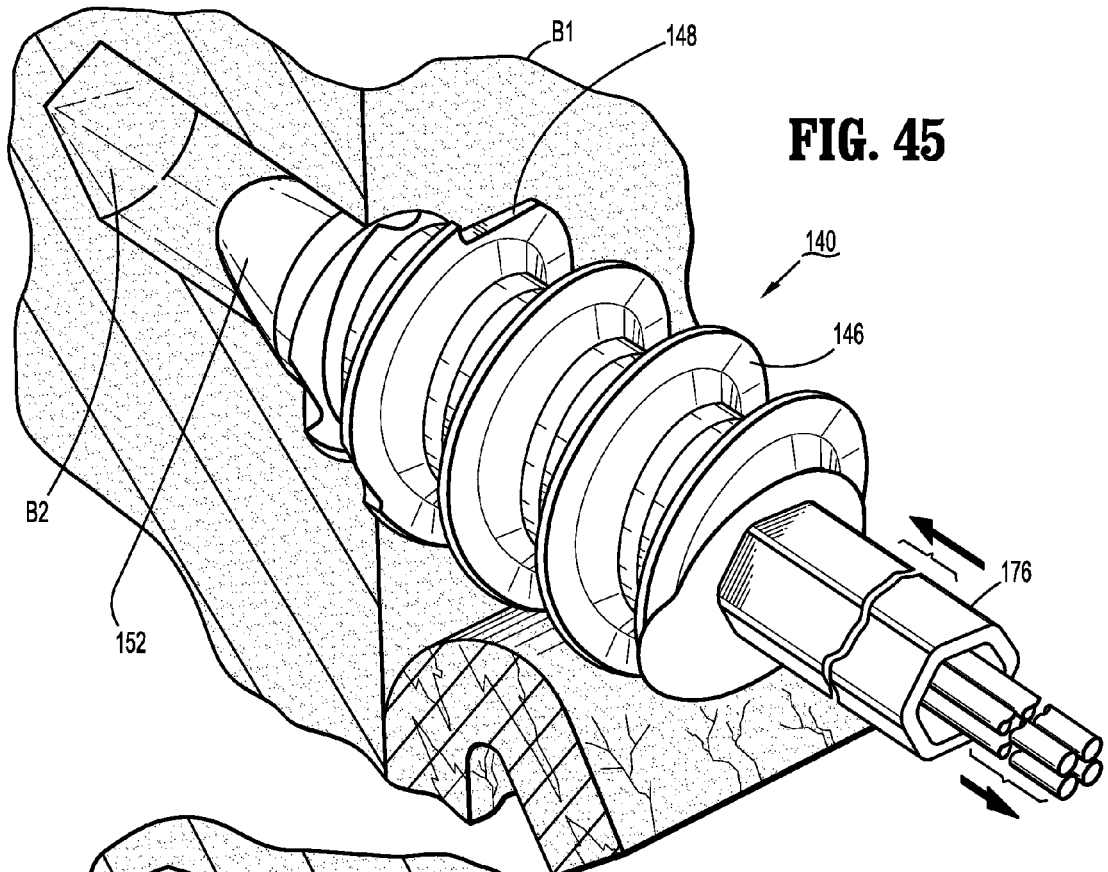
FIG. 45 is a perspective view, partially shown in section, illustrating the suture anchor being inserted into bone.

Slots 160A and B communicate with each other through a crossbore 164. Similarly, slots 162A and B are in communication with each other through a crossbore 166. As best shown in FIG. 41, crossbores 164 and 166 extend parallel to each other through shaft 154. Additionally, crossbores 164 and 166 are located at the same longitudinal location along shaft 154. Shaft 154 has a hexagonal cross-section to mate with the hexagonal bore 150 of threaded outer member 142 to prevent any rotation of insert 144 relative to threaded outer member 142 during the tensioning of sutures.

Hexagonal bore 150 is also provided to engage a hexagonal driver at its proximal end.

Referring to FIG. 43, in order to assembly two-part, non-cannulated suture anchor 140 prior to use, a pair of sutures 168 and 170 are positioned through hexagonal bore 150 and crossbores 162 and 164. Specifically, a first free end 172A of suture 168 is threaded through bore 150 and through crossbore 164 and back out bore 150, as shown. Suture 168 also includes a second free end 172B for attachment to tissue. Similarly, suture 170 is installed by inserting a free end 174A through bore 150 and through crossbore 156, such that first free end 174A extends back out of hexagonal bore 150. Suture 170 is also provided with a second free end 174B for attachment to tissue.

Referring to FIG. 44, once the sutures have been threaded through suture anchor 140, insert 144 can be drawn into hexagonal bore 150 of threaded outer member 142. Proximal tension on sutures 168 and 170 retain insert within threaded outer member 142. In a specific embodiment, free ends 172A and B and free ends 174A and B of sutures 168 and 170, respectively, are then threaded through the interior of a hexagonal driver 176.

Figure 46:
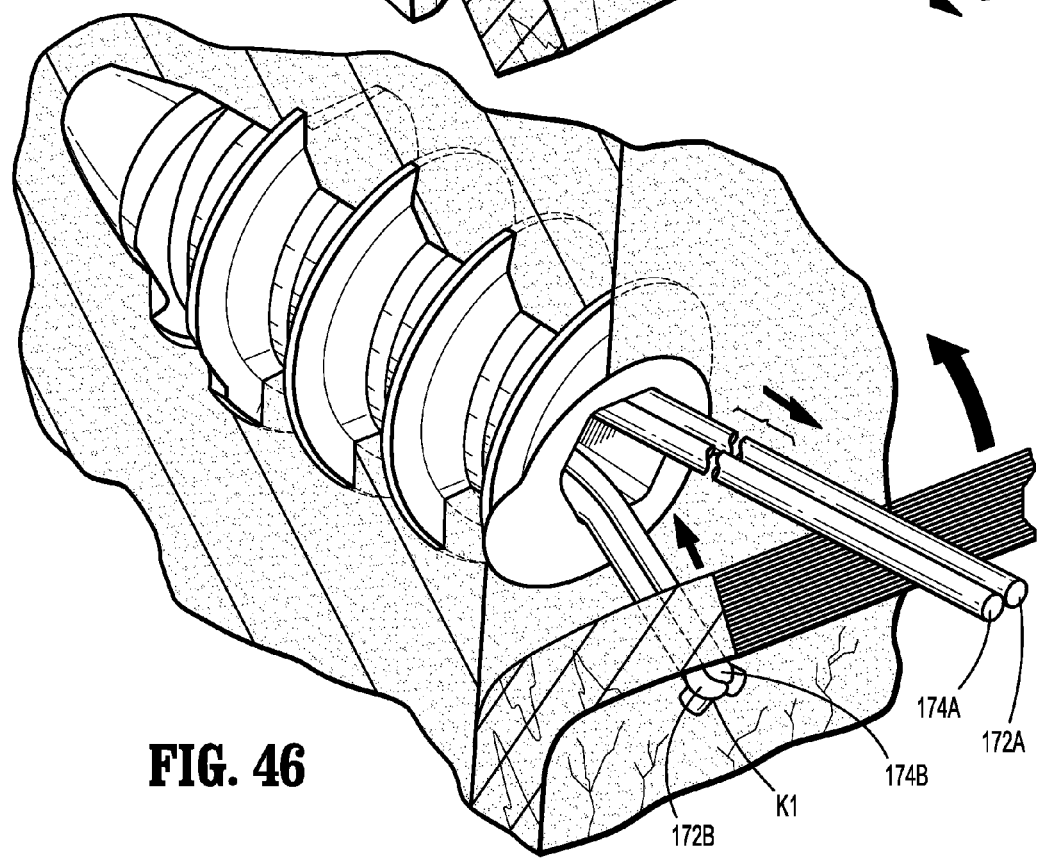
FIG. 46 is a perspective view illustrating the suture anchor with the sutures being tensioned.

Referring now to FIGS. 45-48, in use, a bore B2 is pre-drilled in bone B1 and driver 176 is used to position conical tip 152 of suture anchor 140 initially within the bore. Thereafter, driver 176 is rotated such that interrupted cutting edges 148 of threads 146 cut a thread into the bone to secure suture anchor 140 within the bone. Once suture anchor 140 has been secured in bone, free ends 172B and 174B are knotted together through tissue T at a knot K1. Thereafter, the opposing free ends 172A and 174A are tensioned to draw tissue T against bone B by pulling on sutures 168 and 170, as best shown in FIG. 46.

Figure 47:
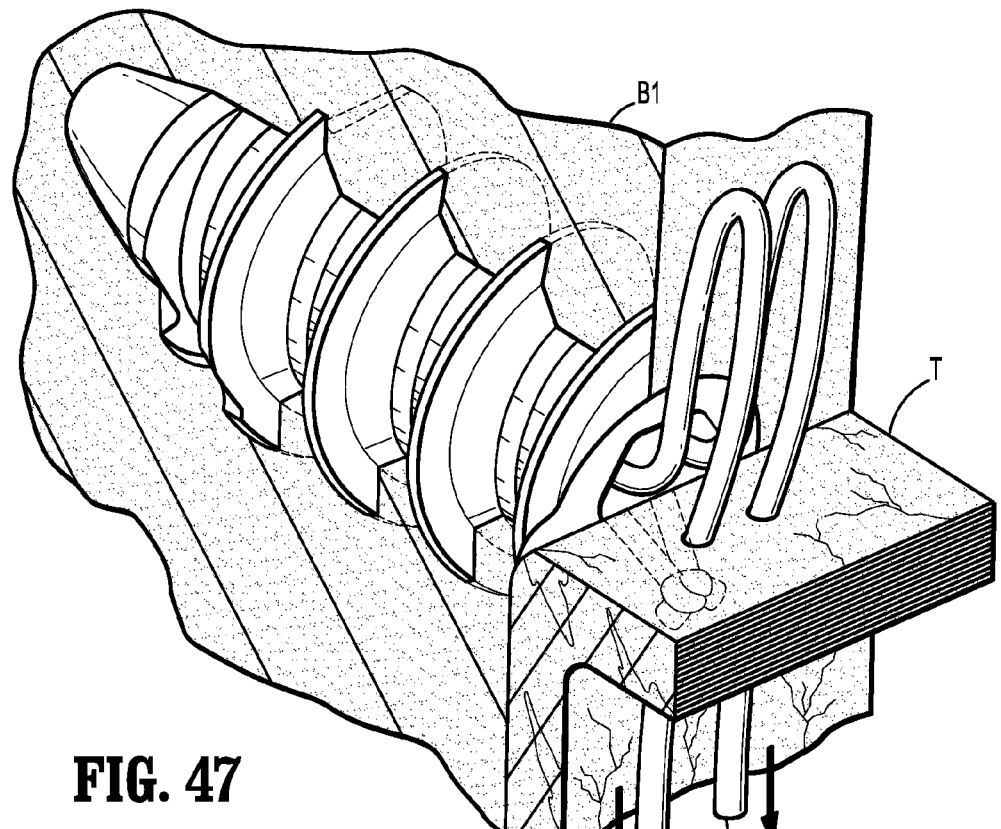
FIG. 47 is a perspective view illustrating tissue being secured by the sutures and the suture anchor.
Figure 48:
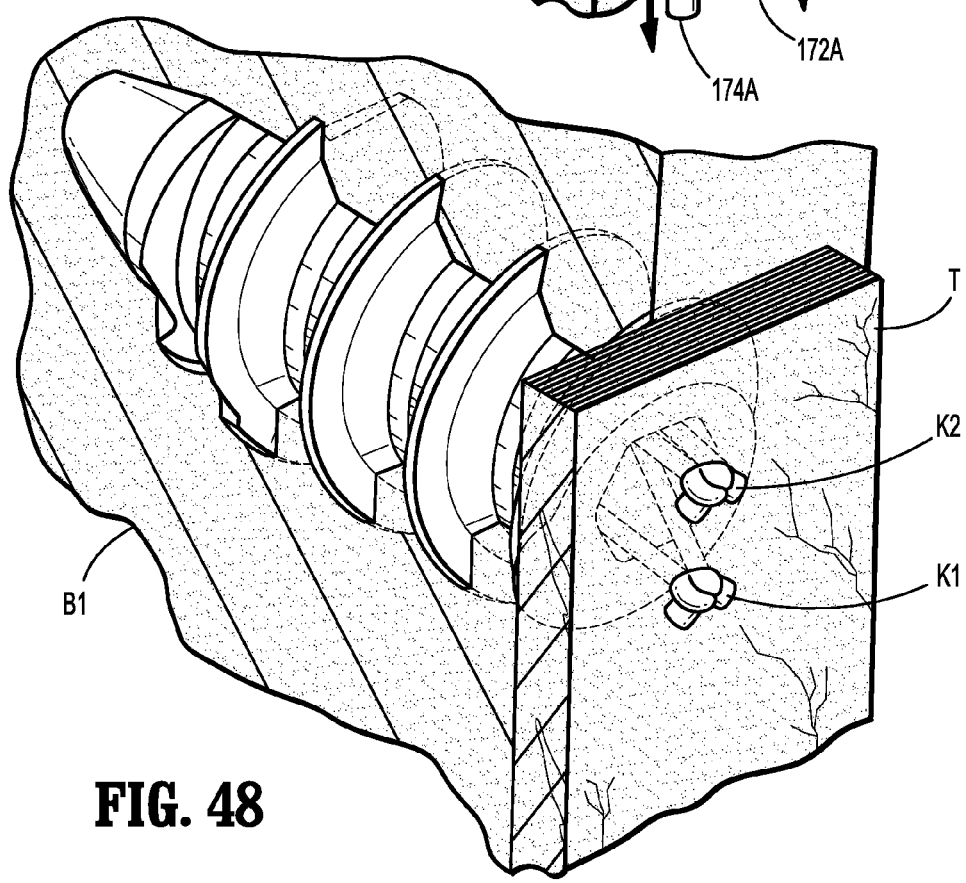
FIG. 48 is a perspective view illustrating the sutures being knotted to secure the tissue.

In one method of use, as best seen in FIGS. 47-48, free ends 172A and 174A are then threaded or positioned through tissue, preferably using a suture needle, and tensioned and knotted at a knot K2 to thereby secure the tissue T to bone B.

While the illustrated use of suture anchor 140 shows the attachment of a flat section of tissue to the surface of a bone B, in an alternative method of use, a longitudinal bore would be cut or drilled into bone B longer than the length of suture anchor 140. The assembled suture anchor 140 would then be inserted deep into the bore in bone and free ends 172B and 174B could be attached to one or more ligaments. Once the ligaments have been attached, the sutures 168 and 170, the opposing free ends 172A and 174A are tensioned to draw the ligaments deep into the bore drilled in bone. This is particularly useful when experimenting with the correct tension on the ligament during surgery, as the depth of the ligament and the bore of bone can be adjusted by tensioning sutures 168 and 170.

Figure 49:
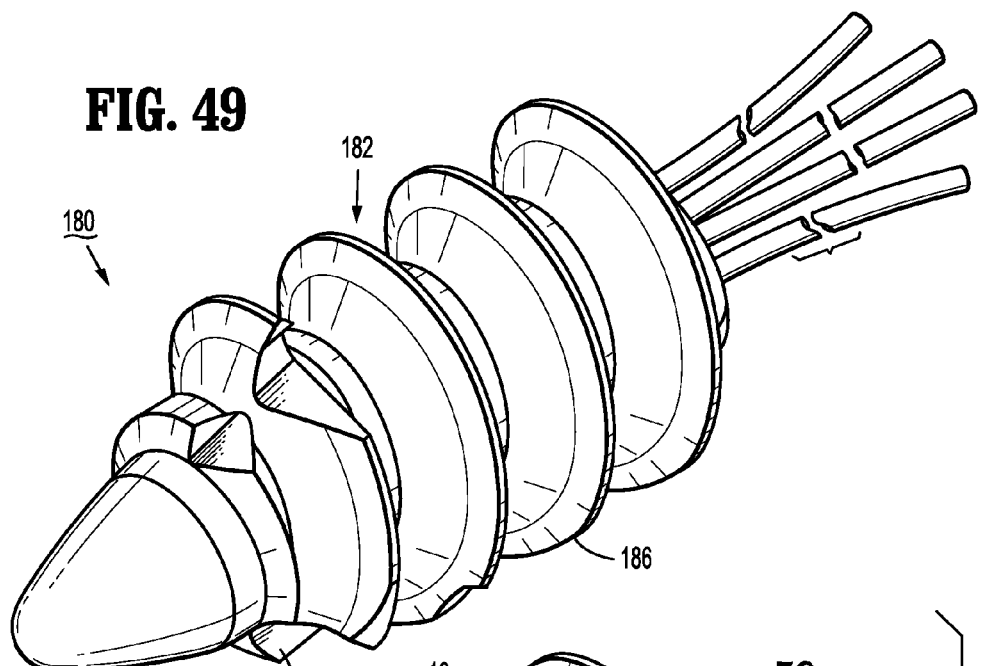
FIG. 49 is a perspective view of another embodiment of a non-cannulated suture anchor.
Figure 50:
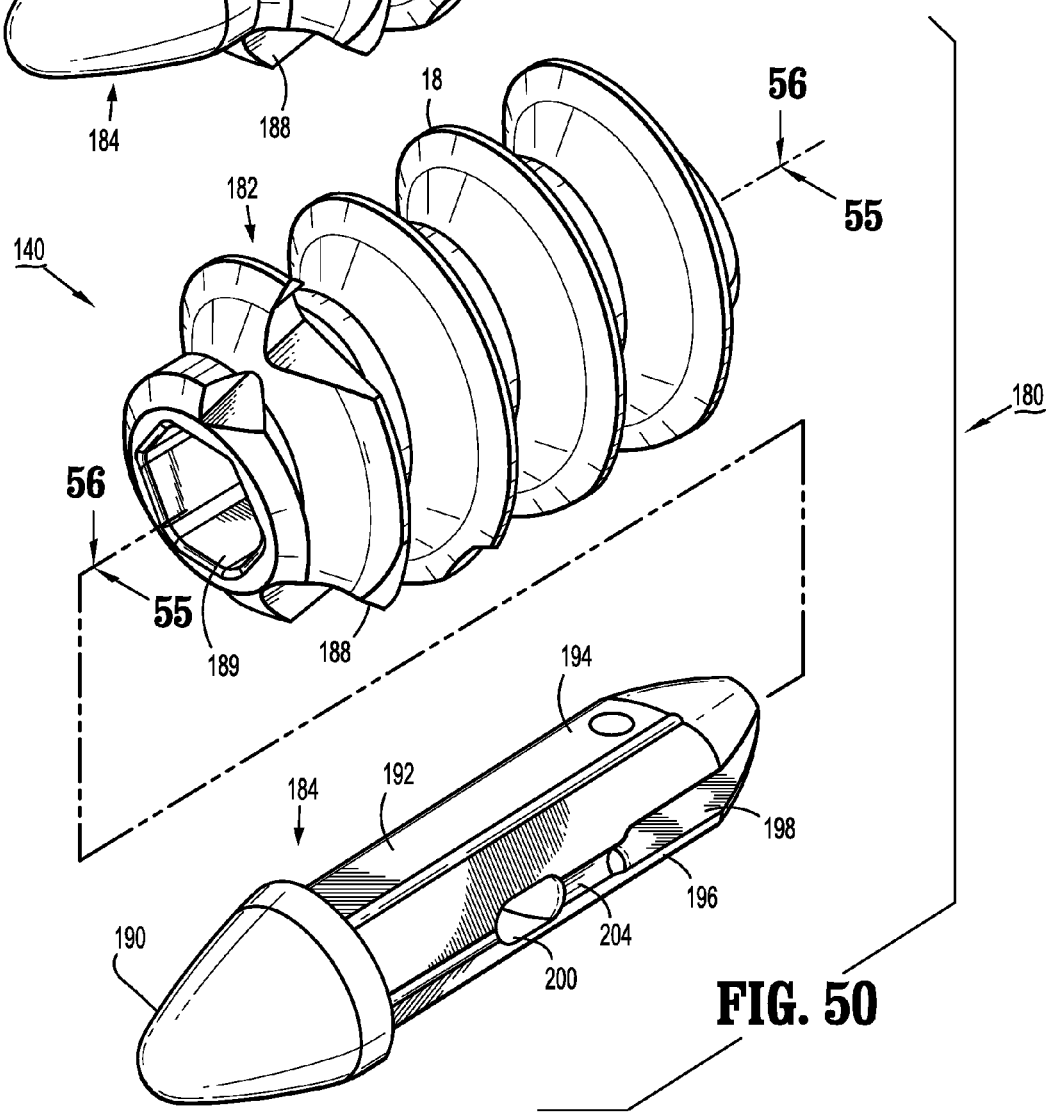
Figure 55:
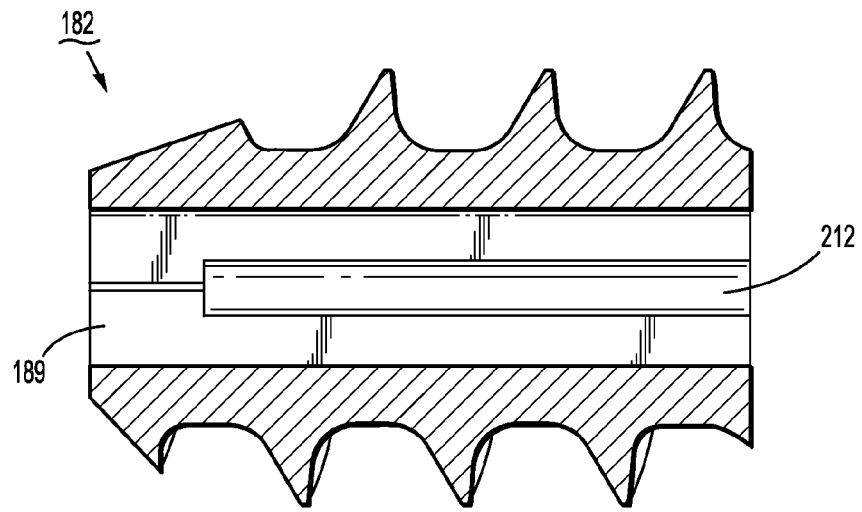
FIG. 55 is a cross-sectional view of the threaded outer member taken along line 55-55 of FIG. 50.
Figure 56:
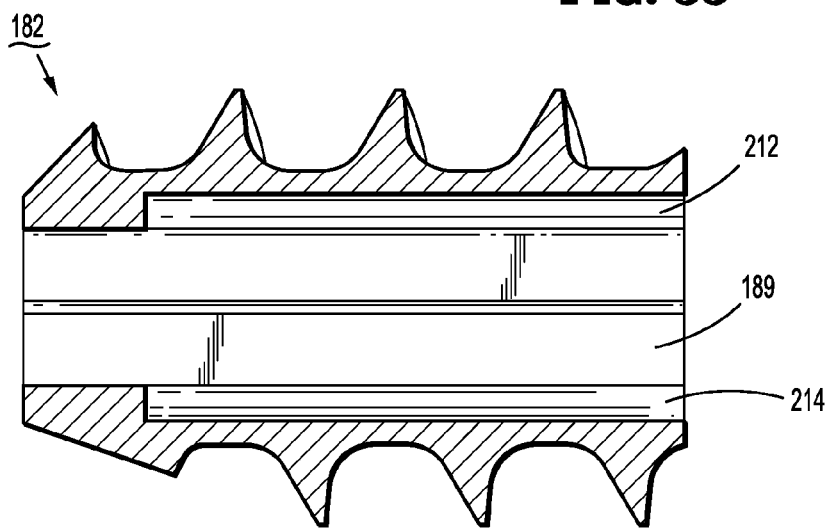
FIG. 56 is a cross-sectional view of the threaded outer member taken along line 56-56 of FIG. 50.
Figure 57:
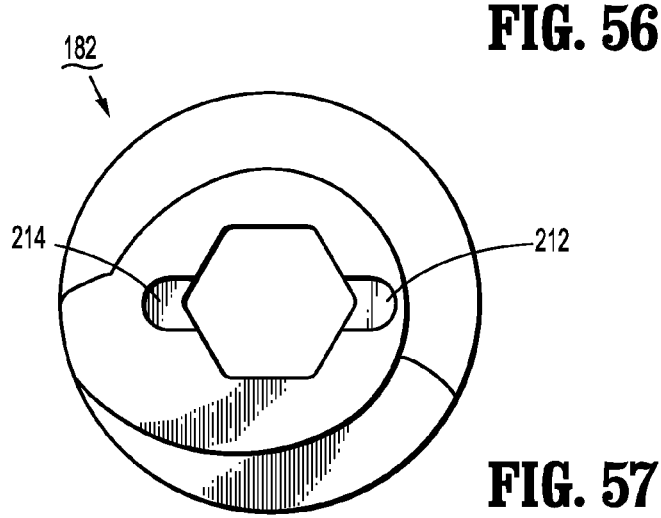
FIG. 57 is an end view of the threaded outer member.

Referring now to FIGS. 49-50, there is disclosed an alternate embodiment of a two part non-cannulated suture anchor. Suture anchor 180 generally includes a hollow body 182 and an insert 184 insertable into hollow body 182. Hollow body 182 is formed with a thread 186 extending circumferentially therearound and includes interrupted cutting edges 188 formed at a distal end of threads 186. Cutting edges 188, as with cutting edges described hereinabove, assist in threading suture anchor 180 into bone. Insert 184 generally includes a smooth atraumatic conical tip 190 having a shaft 192 extending proximally therefrom. Shaft 192 has a hexagonal cross section so as to mate with the hexagonal cross section of a bore 189 formed in hollow body 182.

As shown, shaft 192 has a pair of proximally extending ears 194 and 196 which together define a slot 198 therebetween. This is to provide a recessed suture track at the proximal end of shaft 194 as will be discussed in more detail hereinbelow. Shaft 192 additionally includes a throughbore 200 and a pair of partial channels 202 and 204 extending proximally from throughbore 200. Channels 202 and 204, along with corresponding channels formed in an inner surface of hollow body 182 and with shaft throughbore 200 define a suture track for receipt and permit movement of a suture therethrough.

Referring to FIGS. 51-54, each ear 194 and 196 includes a hole 206 and 208 for receipt of a pin 210 therethrough. Pin 210 is provided to act as a turn around point for a suture positionable within slot 198. With reference to FIGS. 51 and 55-57, hollow body 182 is provided with a pair of partial channels 212 and 214 formed along an inner surface of bore 189. Partial channels 212 and 214 extend from a proximal end of hollow body 182 distally to a point short of the distal end of hollow body 182. Specifically, the distal most end of partial channels 212 and 214 are positioned to correspond to the position of throughbore 200 formed in insert 184. In this manner channels 202 and 204 combine with channels 212 and 214 to form a complete circumferential channel extending proximally within each side of cannulated suture anchor 180 for slidable receipt of a suture therethrough.

Figures 58, 59:
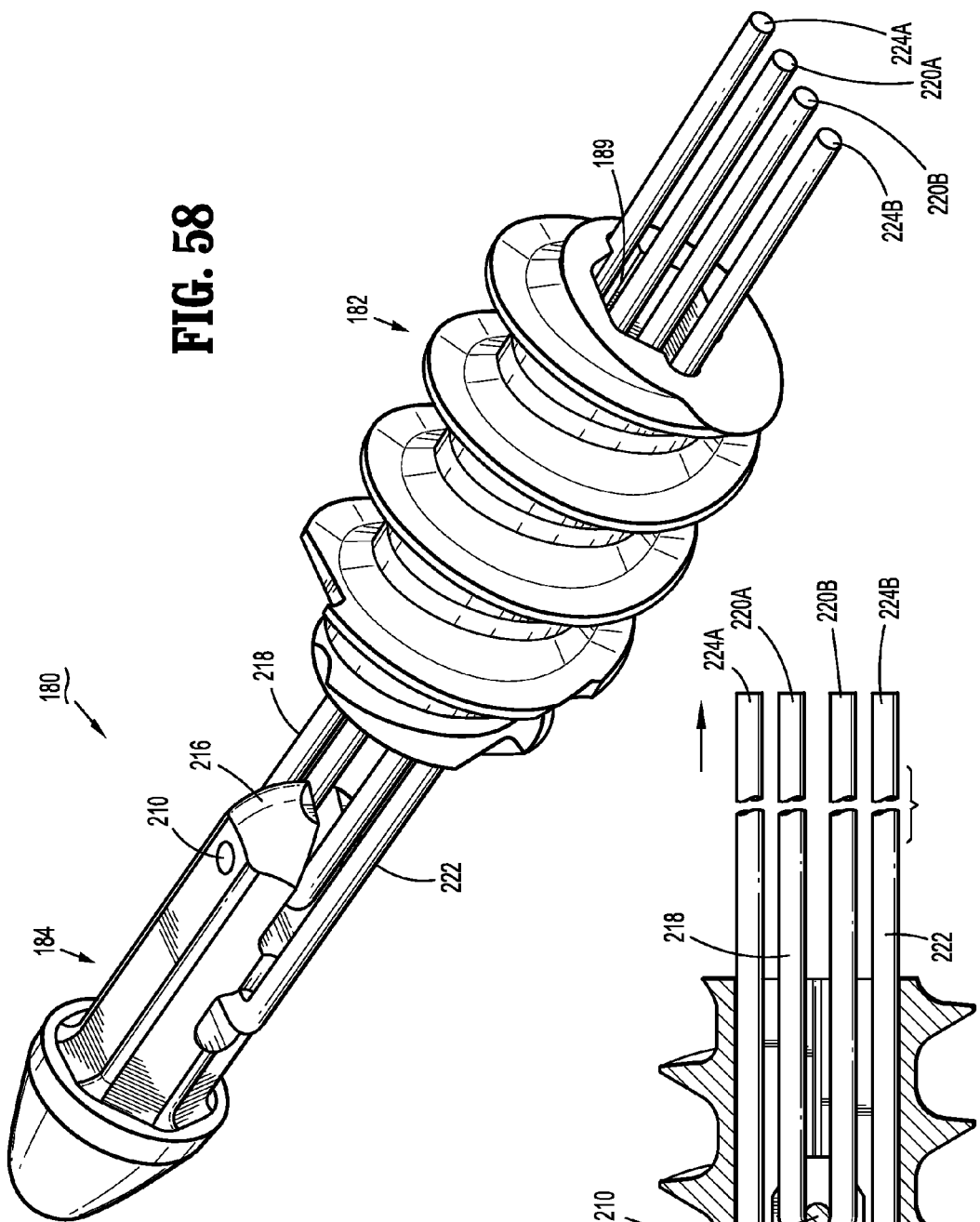
FIG. 58 is a perspective view illustrating the suture anchor being assembled with sutures.
FIG. 59 is a cross-sectional view illustrating the suture anchor being assembled with sutures.

Referring now to FIGS. 58-59, in order to assembly suture anchor 180 prior to use, sutures need to be positioned through hollow body 182 and within the suture tracks defined by insert 184. As with prior embodiments, shaft 192 is provided with a tapered proximal end 216 to facilitate insertion of shaft 182 within bore 189 of hollow body 182. Initially, a first suture 218 having free ends 220 A and B is inserted through bore 189 in hollow body 182 such that the suture passes around pin 210 and extends proximally within slot 198 defined by ears 194 and 196. As best shown in FIG. 59, suture 218 follows a generally radially inner suture track or path within suture anchor 180. A second suture 222 having free ends 224A, B is also positioned through bore 189 of hollow body 182. Specifically, suture 222 extends along partial channel 212 in hollow body 182 and through throughbore 200 in shaft 192 and back proximally along partial channel 214 in hollow body 182. As noted above, channels 202 and 204 in shaft 192 cooperate with partial channels 212 and 214 in hollow body 182 to form a complete circumferential channel for receipt and passage of suture 222. Again as best seen in FIG. 59, suture 222 takes a generally radially outward suture track or path through suture anchor 180 relative to the path taken by suture 218.

The use of suture anchor 180 to be installed into bone and to secure tissue adjacent or within bone is substantially similar to that described hereinabove with respect to prior embodiments and will not be described further herein.

Figure 60:
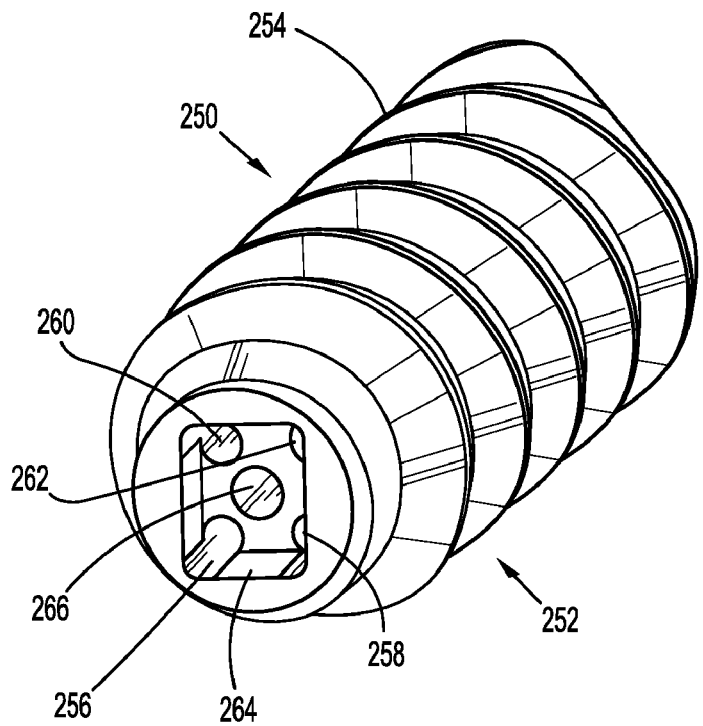
FIG. 60 is a perspective view of an additional embodiment of the suture anchor of the present disclosure.
Figure 61:
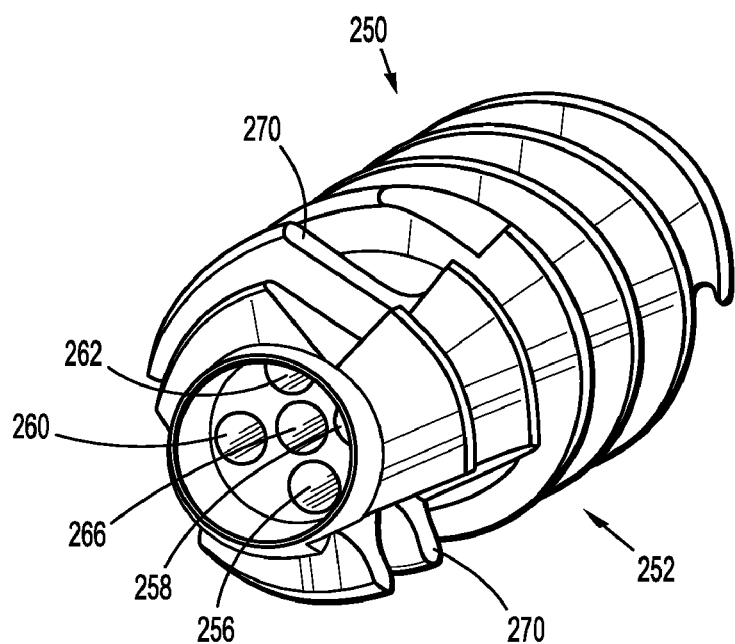
FIG. 61 is a perspective view of yet another embodiment of the suture anchor of the present disclosure.

FIGS. 60-61 illustrate further embodiments of suture anchor 250. In FIG. 60, the outer body 252 is provided with an uninterrupted circumferential thread 254 which extends the length of the anchor 250. Four longitudinally extending bores 256, 258, 260 and 262 are formed in the outer body 252 and are configured to receive sutures therein. As in previous embodiments, the sutures are looped with the suture ended extending proximally. A substantially square cavity 264 is defined in a distal end of the outer body and accommodates the suture loops. Outer body 250 further defines a guidewire bore 266 oriented longitudinally and extending adjacent bores 256, 258, 260 and 262. The guidewire bore 266 is configured to facilitate placement of the suture anchor 250 over a guidewire.

FIG. 61 shows a suture anchor 250 that is substantially similar to the suture anchor of FIG. 60 with the exception that the thread 254 is interrupted by cutting edges 270 which facilitates cutting into bone. The cavity 272 defined in the distal end of the outer body 252 is substantially circular rather than square.

Figure 62:
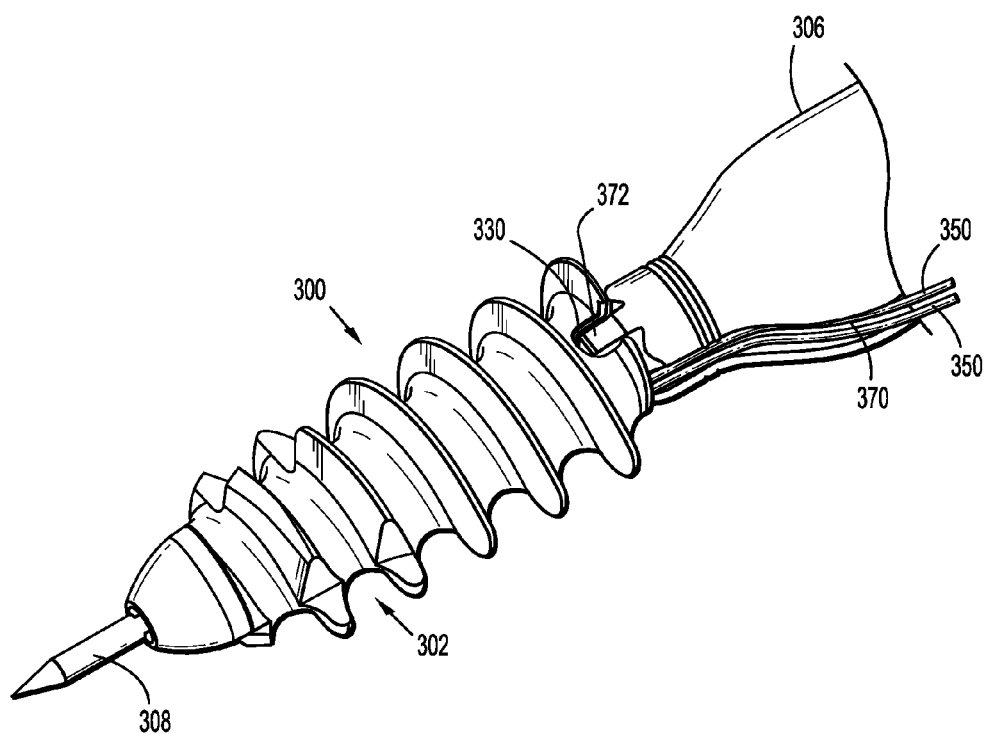
FIG. 62 is a perspective view of a suture anchor system in accordance with the principles of the present disclosure including a suture anchor, anchor driver and guide wire.
Figure 63:
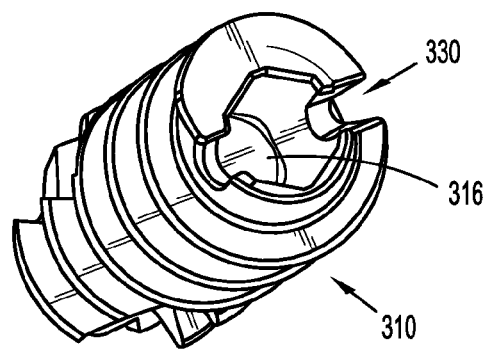
FIG. 63 is a perspective view of the outer sleeve of the suture anchor of the suture anchor system of FIG. 62.
Figure 64:
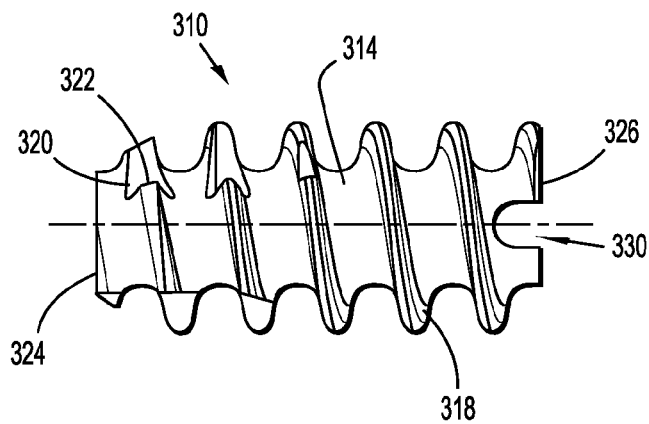
FIG. 64 is a side plan view of the outer sleeve of the suture anchor.
Figure 65:
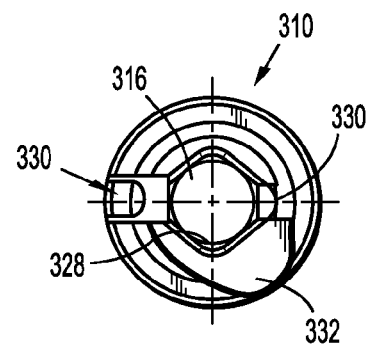
FIG. 65 is an axial plan view of the outer sleeve of the suture anchor.
Figure 66:
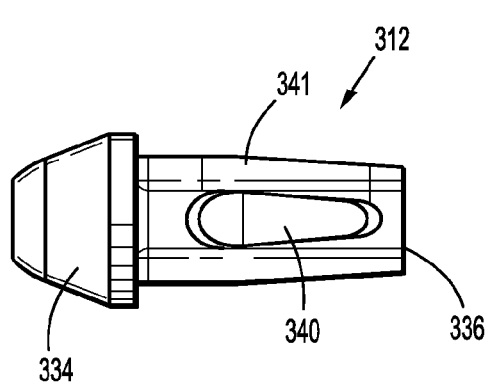
FIGS. 66-67 are side plan views of the insert of the suture anchor.
Figure 67:
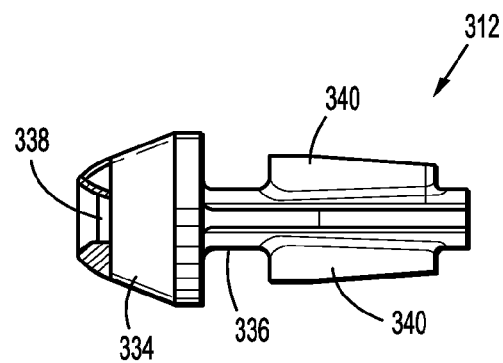

Referring now to FIGS. 62-76, there is illustrated a suture anchor system in accordance with one preferred embodiment of the present disclosure. Suture anchor system 300 includes several components, namely, suture anchor 302, guide wire punch 304, anchor driver 306 and guide wire 308. In FIG. 62, suture anchor 302 is shown mounted to anchor driver 306 with guide wire 308 extending through the suture anchor 302 and the anchor driver 306. Guide wire punch 304 is shown in FIG. 68.

With reference now to FIGS. 63-67, taken in conjunction with FIG. 62, suture anchor 302 includes outer sleeve 310 and insert 312 which is at least partially positionable within the outer sleeve 310. Outer sleeve 310 defines outer wall 314 having longitudinal bore 316 extending therethrough. Outer wall 310 has a continuous helical thread 318. Helical thread 318 has removed or cut out portions 320 which define cutting edges 322. Cutting edges 322 assist in advancing suture anchor 302 within bone. Outer wall 310 further defines leading and trailing ends 324, 326 respectively. Trailing end 326 has a hexagonal opening 328 which receives anchor driver 306. Trailing end 326 further defines diametrically opposed grooves 330 and a contoured or chamfered surface 332. Contoured surface 332 may accommodate portions of the suture extending through suture anchor 302.

Insert 312 defines conical head 334 and insert shaft 336 extending from the conical head 334. Insert 312 defines a longitudinal bore 338 which extends through conical head 334 and through insert shaft 336. Insert shaft 336 has a pair of diametrically opposed rails 340 about which the suture portions are wrapped in a manner which is substantially similar to that described in connection with the embodiment of FIGS. 2-3. Insert 312 further defines alignment fins 341 which are received within corresponding alignment slots (see slots 43 of FIG. 9) within outer sleeve 310.

Referring now to FIGS. 68-71, guide wire punch 304 will be discussed. Guide wire punch 304 is intended to facilitate insertion of guide wire 308 through the tissue and into the bone. Guide wire punch 304 includes punch shaft 342, impactor cap 344 which is mounted to trailing end 346 of the punch shaft 342 and longitudinal bore 348 extending through the punch shaft 342 and the impactor cap 344. Punch shaft 342 defines leading punch tip 350 adjacent leading end 352 of the punch shaft 342. Leading punch tip 352 includes tapered surface 354 extending to cylindrical surface 356. Adjacent trailing end 346, punch shaft 342 includes a pair of leading and trailing transverse grooves 358, 360, respectively which are interconnected by longitudinal groove 362.

Figure 72:
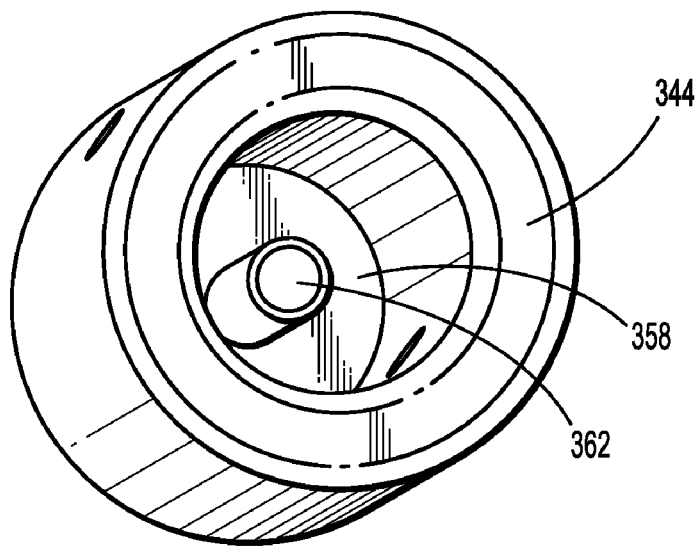
FIG. 72 is a perspective view of the impactor cap of the guide wire punch of FIG. 68.
Figure 73:
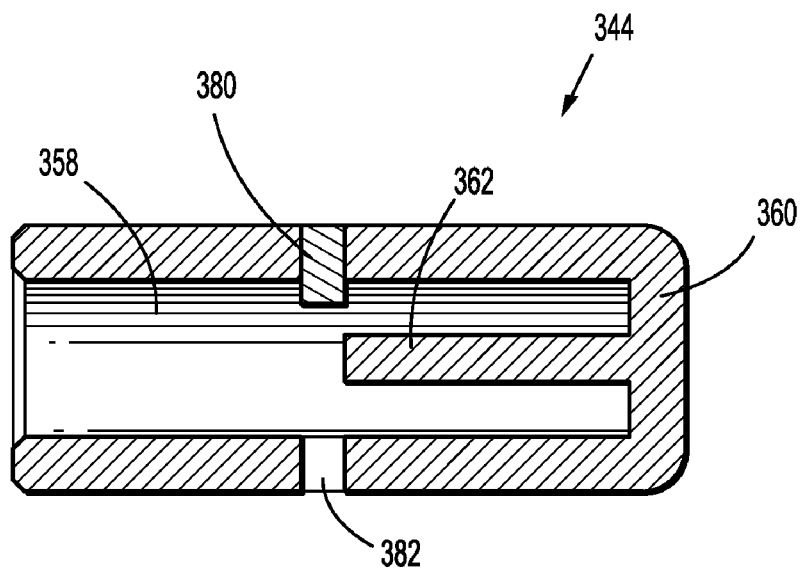
FIG. 73 is a side cross-sectional view of the impactor cap of FIG. 72.

As best depicted in FIGS. 72-73, impactor cap 344 defines longitudinal opening 358 which is dimensioned for positioning over punch shaft 342, and trailing end wall 360. Trailing end wall 360 has internal pin 362 extending within longitudinal opening 358. Internal pin 362 is arranged to be received within longitudinal bore 348 of punch shaft 342 and engage guide wire 308 disposed within the longitudinal bore 348. In this regard, as impactor cap 344 is advanced onto punch shaft 342, internal pin 362 advances guide wire 308 relative to guide wire punch 304 to embed the distal end of the guide wire 308 within the bone. Impactor cap 344 further includes cam pin 380 (FIG. 73). Cam pin 380 extends through one of transverse openings 382 defined in impactor cap 344 and is received within grooves 358, 360, 362 on the exterior of punch shaft 342. Two cam pins 380 may be provided. Cam pin 380 is adapted to traverse grooves 358, 360, 362 when impactor cap 344 is positioned and advanced on punch shaft 342. In this manner, impactor cap 344 may be selectively positioned on punch shaft 342 between one of two positions, i.e., a first or retracted position where cam pin 380 is received within proximal groove 360 and a second advanced position where cam pin 380 is received in distal groove 358. Thus, the surgeon may be able to selectively control the depth of advancement of internal pin 362 of impactor cap 344 to thereby control the depth or degree of advancement of guide wire 308 relative to punch shaft 342 and the tissue.

Figure 74:
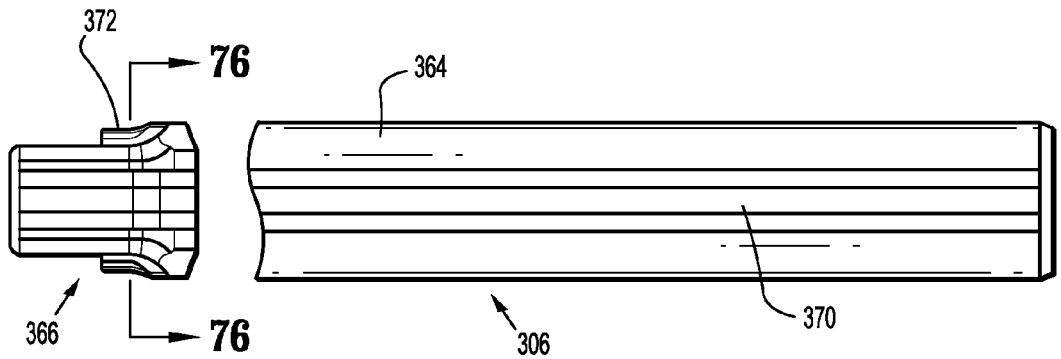
FIG. 74 is a side plan view of the driver of the suture anchor system of FIG. 62.
Figure 76:
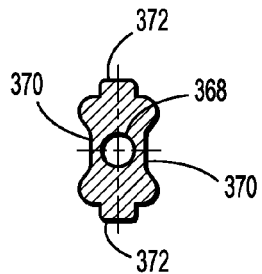
FIG. 76 is a cross-sectional view of the driver tip of the driver taken along line 76-76 of FIG. 74.
Figure 75:
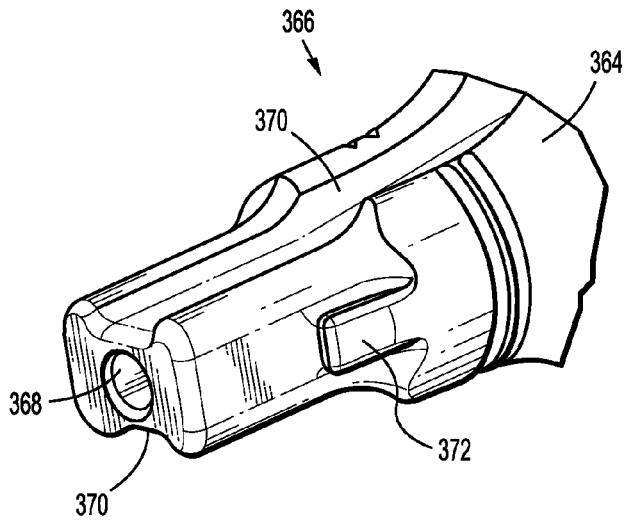
FIG. 75 is an enlarged perspective view of the driver tip of the driver of FIG. 74.

Referring now to FIGS. 74-76, anchor driver 306 will be discussed. Anchor driver 306 includes driver shaft 364, driver tip 366 disposed at the distal end of the driver shaft 364 and longitudinal bore 368 extending through the driver shaft 364 and the driver tip 366. Anchor driver 306 further defines a pair of diametrically opposed grooves 370 which extend along the outer surface of driver tip 366 and along a major portion of the driver shaft 364. Grooves 370 are dimensioned to accommodate suture portions extending back from suture anchor 302. Driver tip 366 further includes a pair of rails 372 offset 90° relative to grooves 370 and spaced from the leading end of driver tip 366. Rails 372 are dimensioned to be received within recesses of grooves 330 of suture anchor 302. In this regard, outer sleeve 310 is coupled to anchor driver 306 whereby rotation of the anchor driver 306 causes corresponding rotation of the outer sleeve 310.

The use of the suture anchor system 300 will now be discussed. Guide wire 308 is positioned within longitudinal bore 348 of guide wire punch 304, and the assembled components are introduced within a cannula accessing a targeted tissue site in a similar manner to the method of use described in connection with FIGS. 14-15. Guide wire punch 304 and guide wire 308 are advanced through the tissue until tapered end of guide wire punch 304 engages bone. Impactor cap 344 is then mounted to punch shaft 342 with internal pin 362 extending within longitudinal bore 348 of guide wire punch 304. In one preferred method, impactor cap 344 is arranged whereby cam pin 380 is received within proximal groove 360 and the impactor cap 344 is tapped to initially advance the guide wire 308 into bone. Thereafter, impactor cap 344 is rotated whereby cam pin 380 is aligned with longitudinal groove 362 of punch shaft 342 and the impactor cap 344 is driven distally to drive and anchor guide wire 308 into bone. Cam pin 380 advances until it engages the wall portion defined by distal groove 360. Other methods are also envisioned. With guide wire 308 positioned within the bone, guide wire punch 308 is removed along the guide wire 308. Suture anchor 302 with loaded sutures 350 is mounted to anchor driver 306 in a manner in which rails 372 of driver tip 366 are received within grooves 330 of outer sleeve 310 as depicted in FIG. 62. Suture anchor 302 and anchor driver 306 are advanced along guide wire 308 until suture anchor 302 engages the bone. Thereafter, anchor driver 306 is rotated to cause corresponding rotation of suture anchor 302 and advancement of the suture anchor 302 within the bone. As appreciated, suture ends of sutures 350 extending back from suture anchor 302 are received within longitudinal grooves 370 of anchor driver 306. The sutures are secured to the tissue in the manner(s) discussed hereinabove to secure the damaged tissue relative to the bone.

Figure 77:
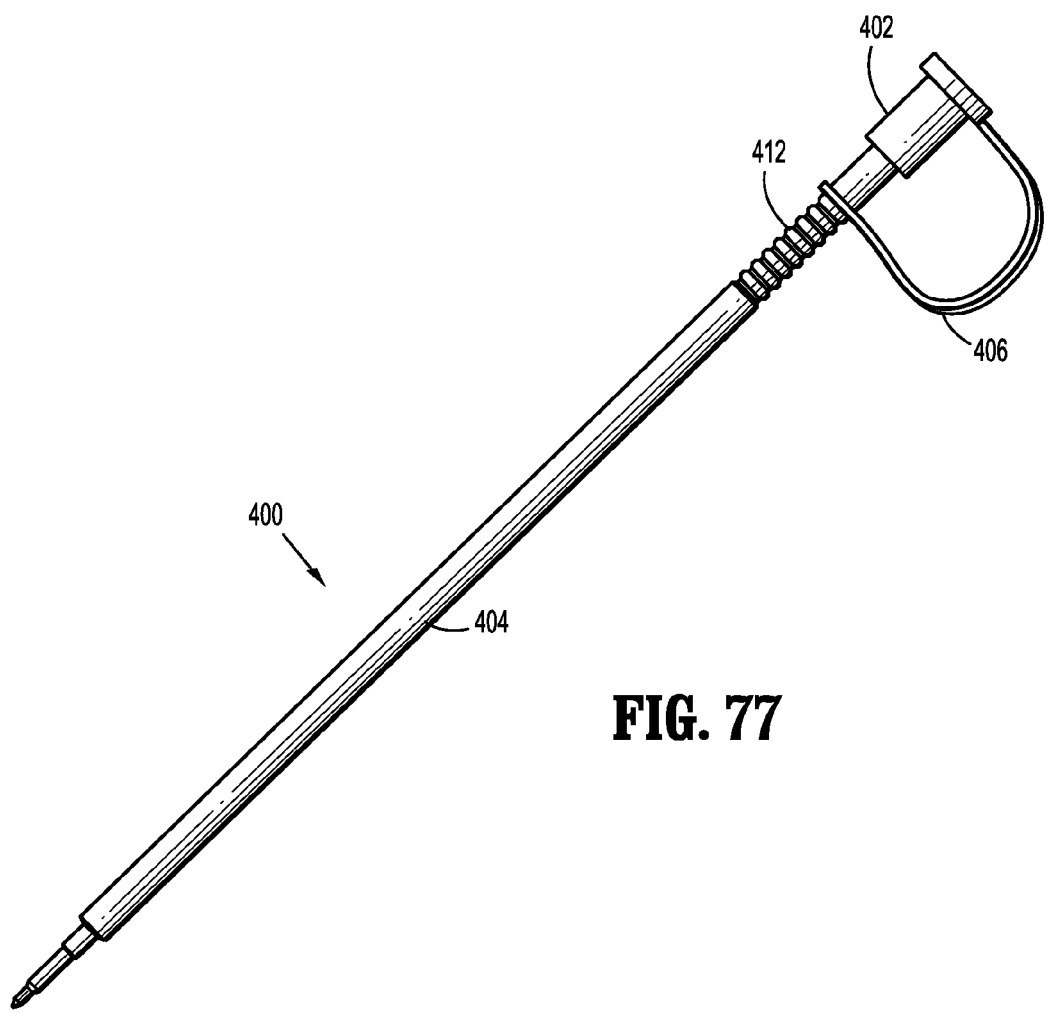
FIG. 77 is a side plan view of an alternate embodiment of a guide wire punch.
Figure 78:
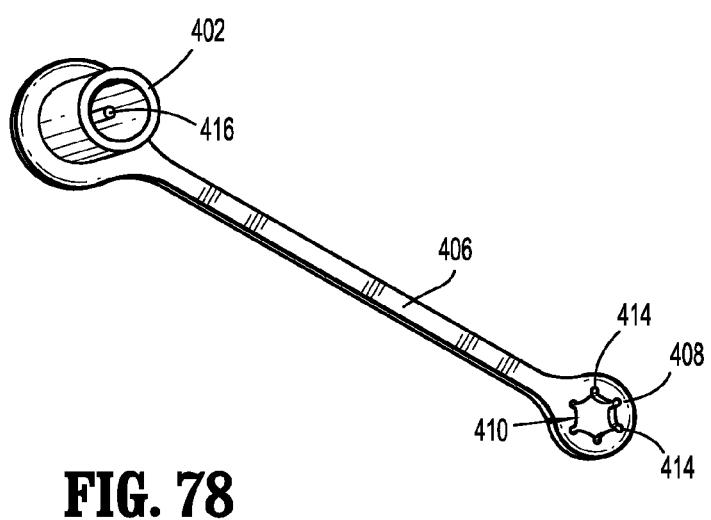
FIG. 78 is a perspective view of an impactor cap of the guide wire punch.
Figure 79:
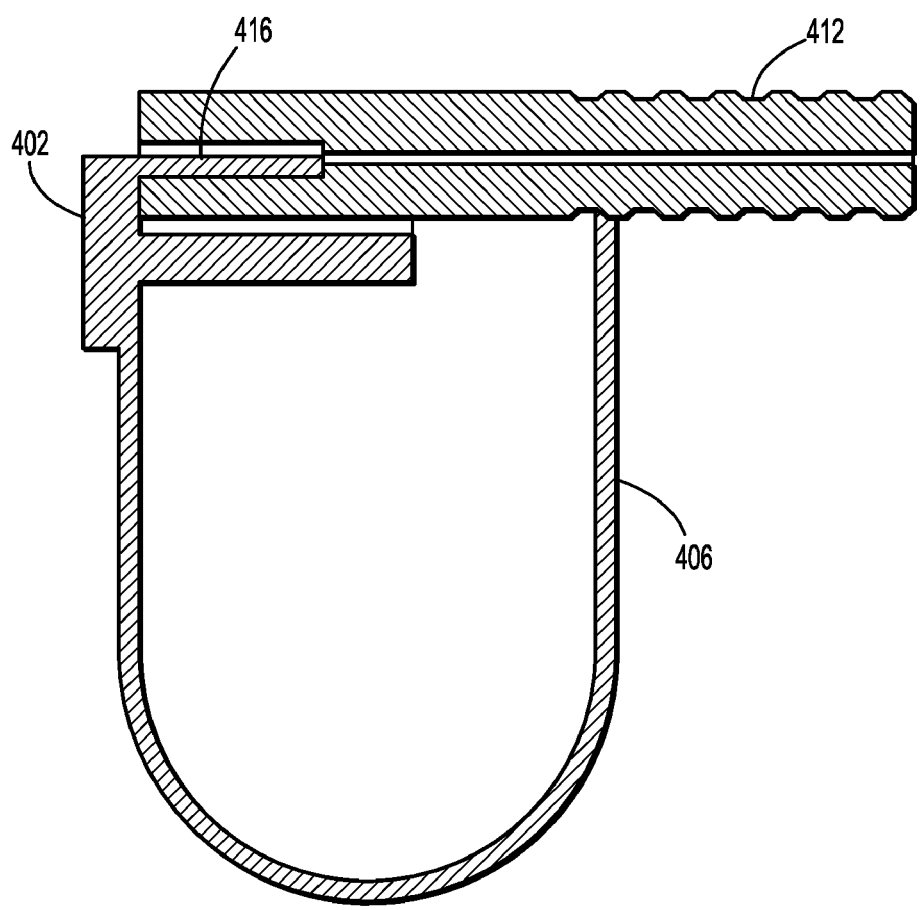
FIG. 79 is a side cross-sectional view illustrating the impactor cap mounted to the punch shaft.

Referring now to FIGS. 77-79, there is illustrated another alternate embodiment of the guide wire punch usable with the system of FIGS. 62-76. Guide wire punch 400 is substantially similar to the guide wire punch described in connection with the embodiment of FIGS. 62-76. However, in accordance with this embodiment, impactor cap 402 is tethered to punch shaft 404 through a tether line 406. In particular, tether line 406 defines connector 408 having aperture 410 which is slid over punch shaft 404 to be received or accommodated within a locking groove 412 defined in the punch shaft 404. Connector 408 defines slits 414 circumscribing aperture 410 which permit the material defining the aperture 410 to flex for reception within one of the locking grooves 412 of punch shaft 404. Impactor cap 402 has internal pin 416 which functions in a similar manner to the corresponding counterpart described in connection with the embodiment of FIGS. 62-76. Preferably, impactor cap 402 and tether line 406 are monolithically formed as a single unit and are preferably fabricated from a flexible polymer material.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A suture anchor, which comprises:
    an outer sleeve having a longitudinal throughbore and defining leading and trailing ends;
    an insert positionable within the longitudinal throughbore of the outer sleeve, the insert having a shaft and at least one suture track extending radially outward from the shaft, the at least one suture track having a leading edge; and
    a suture wrapped around the leading edge of the at least one suture track, whereby opposed free ends of the suture extend from the at least one suture track through the longitudinal throughbore to extend beyond the trailing end of the outer sleeve to be tensioned and secured relative to the tissue.

2. The suture anchor according to claim 1 wherein the outer sleeve includes an external thread.

3. The suture anchor according to claim 1 wherein the insert includes a pair of suture tracks for supporting a pair of sutures.

4. The suture anchor according to claim 1 wherein the insert is operatively connected to the outer sleeve whereby rotation of the outer sleeve causes corresponding rotation of the insert.

5. The suture anchor according to claim 1 wherein the insert includes a shaft and a relatively enlarged leading tip, the shaft being receivable within the longitudinal throughbore of the outer sleeve, the leading tip having a dimension greater than a corresponding dimension of the longitudinal throughbore to be external of the outer sleeve.

6. The suture anchor according to claim 5 wherein the leading tip of the insert defines a conical portion.

7. The suture anchor according to claim 1 wherein the insert is entirely positioned within the longitudinal throughbore of the outer sleeve.

8. The suture anchor according to claim 7 wherein the outer sleeve has at least one longitudinal slot at a distal end thereof such that the insert is positionable within the throughbore and the slot.

9. A suture anchor system, which comprises:
   a suture anchor including:
      an outer sleeve having trailing and leading ends and an external thread;
      an insert at least partially positioned within the outer sleeve, the insert having a shaft and a pair of suture tracks extending radially outward from the shaft, each of the air of suture tracks having a leading edge; and
      a air of sutures each suture wrapped around the leading edge of one of the suture tracks and having suture end portions extending through the outer sleeve and out the trailing end thereof; and
   an anchor driver for installing the suture anchor in tissue, the anchor driver including a driver shaft and a driver tip, at least the driver shaft having a pair of longitudinal recesses defined in an outer surface thereof for reception of respective suture end portions extending from the outer sleeve, the driver tip being operatively engageable with the outer sleeve of the suture anchor whereby rotational movement of the anchor driver causes corresponding rotational movement of the outer sleeve and advancement of the suture anchor into the tissue.

10. The suture anchor system according to claim 9 wherein the insert of the suture anchor includes a longitudinal bore extending therethrough for reception and passage of a guide wire.

11. The suture anchor system according to claim 10 wherein the anchor driver includes a longitudinal bore therethrough for reception and passage of a guide wire.

12. The suture anchor system according to claim 9 including a guide wire punch for facilitating entry of a guide wire into the tissue, the guide wire punch including a punch shaft defining a longitudinal bore for reception and passage of a guide wire and an impactor cap mountable to the punch shaft, the impactor cap having an internal pin dimensioned to be received within the longitudinal bore of the punch shaft when the impactor cap is mounted to the punch shaft whereby advancement of the impactor cap onto the punch shaft causes the internal pin to engage and drive the guide wire into the tissue.

13. The suture anchor system according to claim 12 wherein the impactor cap is tethered to the punch shaft with a tether line.

14. The suture anchor system according to claim 13 wherein the impactor cap and the tether line are formed of a polymeric material.

* * * * *

UNITED STATES PATENT AND TRADEMARK OFFICE
CERTIFICATE OF CORRECTION

PATENT NO. : 7,588,587 B2  Page 1 of 1
APPLICATION NO. : 11/371821
DATED : September 15, 2009
INVENTOR(S) : Barbieri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 536 days.

Signed and Sealed this

Twenty-first Day of September, 2010

David J. Kappos
*Director of the United States Patent and Trademark Office*